United States Patent
Dederen et al.

(10) Patent No.: US 6,831,107 B2
(45) Date of Patent: Dec. 14, 2004

(54) EMULSIFICATION SYSTEMS AND EMULSIONS

(76) Inventors: Christian Joseph Dederen, Dorpstraat 144A, Meerbeek (BE), B-3078; Thierry Wetzel, 106 Rue Gallait, Brussels (BE), B-1030; Guido Serrien, Duisburgsesteenweg 69, Tervuren (BE), B-3080

( * ) Notice: Subject to any disclaimer, the term of this patent is extended or adjusted under 35 U.S.C. 154(b) by 0 days.

(21) Appl. No.: 09/865,296

(22) Filed: May 29, 2001

(65) Prior Publication Data

US 2002/0065328 A1 May 30, 2002

Related U.S. Application Data

(63) Continuation of application No. 09/452,144, filed on Dec. 1, 1999, now abandoned
(60) Provisional application No. 60/111,440, filed on Dec. 8, 1998.

(30) Foreign Application Priority Data

Dec. 5, 1998 (GB) .............................................. 9826699

(51) Int. Cl.$^7$ .......................... A01N 25/04; A61K 7/00; A61K 47/36
(52) U.S. Cl. ....................... 514/777; 514/939; 514/941; 514/772; 514/782; 516/73; 516/74; 516/107; 424/401; 424/78.3; 424/59
(58) Field of Search .............................. 516/73, 74, 76, 516/107; 424/401, 59, 78.3; 514/939, 941, 23, 54, 777, 782, 772

(56) References Cited

U.S. PATENT DOCUMENTS 4,676,976 A * 6/1987 Toba et al. ................. 516/107
5,498,436 A * 3/1996 Modliszewski et al. ..... 426/573
5,624,612 A * 4/1997 Sewall et al. ................ 264/4.1
6,042,815 A * 3/2000 Kellner et al. .............. 424/401

FOREIGN PATENT DOCUMENTS

| CA | 2188331 | 4/1997 |
| EP | 0 208 313 | 1/1987 |
| GB | 2 137 066 A | * 10/1984 |
| WO | WO 93/02571 | * 2/1993 |
| WO | WO 96/31187 | * 10/1996 |
| WO | 98/19553 | 5/1998 |

OTHER PUBLICATIONS

"More stable gums added to xanthan gum", Manufacturing Chemist, vol. 63, No. 2, Feb. 1992, p. 43.

* cited by examiner

*Primary Examiner*—Daniel S. Metzmaier
(74) *Attorney, Agent, or Firm*—Mayer Brown Rowe & Maw LLP

(57) ABSTRACT

Personal care or cosmetic oil in water emulsions include an oil emulsifier and a combination of a Xanthan polysaccharide and a polyglucomannan polysaccharide to provide enhanced stability even at low emulsifier stabiliser levels. The emulsifier stabiliser system provides stable emulsions without dominating system rheology, particularly viscosity. Thus, the emulsions can have a low viscosity suitable for formulation as milks or thin lotions, or can be thickened, desirably by thickening agents other than the Xanthan and/or polyglucomannan, to provide emulsion creams or gels. This enables the system to be used very flexibly in end use applications. The emulsifier is desirably a non-ionic emulsifier and particularly is a combination of a low HLB and a high HLB emulsifier and can be formulated with conventional alcohol ethoxylate surfactants or from non-EO surfactants e.g. sucrose ester high HLB surfactants and citrate or sorbitan ester low HLB surfactants.

43 Claims, No Drawings

EMULSIFICATION SYSTEMS AND EMULSIONS

This application is a continuation of U.S. application Ser. No. 09/452,144, which was filed on Dec. 1, 1999, now abandoned. This application claims the benefit of U.S. Provisional Patent Application No. 60/111,440, which was filed on Dec. 8, 1998. This application also claims the benefit of priority of Great Britain Patent Application No. 9826699.2, filed on Dec. 5, 1998. This application is also related to PCT application number PCT/GB99/03969, filed Nov. 29, 1999.

This invention relates to emulsification systems and emulsions and in particular to emulsification systems including emulsifiers and high molecular weight polysaccharide combinations and to emulsions made using such systems as emulsifiers and emulsion stabilisers and particularly to such emulsification systems and emulsions in the form of personal care products such as cosmetic skin creams and milks.

Personal care emulsion products such as creams and milks desirably have a number of properties in combination: stability in manufacture, formulation, storage and use; a viscosity appropriate to the end use; and preferably a desirable body and good skin feel. Body and skin feel are usually assessed subjectively, and although good body and/or skin feel are commonly associated with a non-Newtonian, shear thinning viscosity profile, a shear thinning profile does not guarantee a good body or skin feel. Typical conventional personal care emulsion products use emulsifiers (including emulsion stabilisers) in amounts of about 3 to about 5% by weight of the emulsion. Recently, thickeners have been proposed as emulsion stabilisers and the mechanism of stabilisation when these are used appears to be that the thickener increases the low shear viscosity of the emulsion sufficiently to provide a barrier to emulsion droplet coalescence, probably by limiting the movement of the droplets.

The present invention is based on our discovery that certain combinations of high molecular weight polysaccharides can provide good emulsion stabilisation at levels that do not give high, or even significantly increased, low shear viscosity and that using such combinations, the amount of emulsifier, usually a relatively low molecular weight, often non-ionic, surfactant can be much less than is used conventionally in emulsions, particularly emulsions for personal care products such as cosmetic skin creams and milks.

The present invention accordingly provides a personal care or cosmetic oil in water emulsion which includes as an emulsifier stabiliser system, an emulsifier for the oil and a polysaccharide combination of a Xanthan polysaccharide and a polyglucomannan polysaccharide.

The invention also includes the use of a polysaccharide combination of a Xanthan polysaccharide and a polyglucomannan polysaccharide as an emulsifier stabiliser system in personal care or cosmetic oil in water emulsions. The invention further includes a dry blend emulsifier stabiliser formulation which includes an oil emulsifier and an oil in water emulsion stabiliser which is a polysaccharide combination of a Xanthan polysaccharide and a polyglucomannan polysaccharide.

The polysaccharide combination of a Xanthan polysaccharide and a polyglucomannan polysaccharide may for convenience briefly referred to as a polysaccharide stabiliser.

The combined amount of emulsifier and stabiliser in emulsions of the invention can be much lower than the typical 3 to 5% used in conventional personal care emulsion systems. In particular, in many emulsions of this invention, the amount of emulsifier can be less than about 1.5%, particularly up to about 1%, and the amount of polysaccharide stabiliser can be less than about 0.5%, and sometimes as little as about 0.02%, desirably with the combined amount being less than about 1.5%, particularly up to about 1%. The minimum amount of emulsifier is typically about 0.02% more usually 0.025% by weight of the emulsion (see also below). Accordingly, the invention includes a personal care or cosmetic oil in water emulsion which includes as an emulsifier stabiliser system an emulsifier for the oil in an amount not more than about 1% by weight of the emulsion and a polysaccharide stabiliser in an amount of from about 0.02 to about 0.5% by weight of the emulsion.

Personal care emulsions can be divided by viscosity into milks and lotions, which typically have a low shear viscosity of up to about 10000 mPa.s, and creams which typically have a low shear viscosity of more than about 20000 mPa.s. Typically, milks and lotions have a low shear viscosity of from about 100 to about 10000 mPa.s, more usually from about 500 to about 5000 mPa.s, and typically creams have a low shear viscosity of at least about 30000 mPa.s, particularly from about 30000 to about 80000 mPa.s, although even higher viscosities e.g. up to about $10^6$ mPa.s, may also be used. In this context low shear viscosity refers to viscosity measured at shear rates of about 0.1 to 10 $s^{-1}$ as is typically used in Brookfield viscometers. Because for good skin feel, personal care and cosmetic emulsions are usually shear thinning, the measured low shear viscosity is only a general guide to whether the product is a milk (or lotion) or cream.

The present invention includes both milk (and lotion) and cream emulsions and specifically the invention includes a personal care or cosmetic oil in water emulsion milk or lotion having a low shear viscosity of up to about 10000 mPa.s, which includes as an emulsifier stabiliser system an emulsifier for the oil and a polysaccharide stabiliser. The invention further includes a personal care or cosmetic oil in water cream emulsion having a low shear viscosity of more than about 20000 mPa.s, which includes as an emulsifier stabiliser system an emulsifier for the oil and a polysaccharide stabiliser, the emulsion further including thickener components.

Xanthan is a polysaccharide including mannose, glucose and glucuronic acid monomer units and typically the main polymer backbone is polyglucose with 3-unit acetylated side chains including glucose, glucuronic acid, typically present as a mixed potassium, sodium and calcium salt, and mannose residues. Xanthan polymers have a molecular weight typically in the range $1.10^6$ to $5.10^6$ and usually about $2.10^6$ and are typically obtained from bacterial fermentations, particularly of *Xanthomannas campestris* and related microorganisms. The Xanthan products sold under the Keltrol tradename, particularly the 'F' and 'T' grades, by Kelco are particularly suitable in this invention.

The polyglucomannan typically has a random glucose/mannose backbone, typically at a molar ratio of glucose to mannose in the range about 1:1.5 to about 1:3, usually about 1:2 with hydroxyl groups on pendent methylol groups randomly acetylated, typically so that there is about one acetyl group per 6 to 20 sugar monomer residues. The molecular weight of useful polyglucomannans can vary within a typical range of from about $2.10^5$ to about $2.10^6$. Suitable materials include vegetable polyglucomannans such as those derived from *Konjak*. *Konjak* polyglucomannan, sometimes referred to simply as *Konjak* or *Konjak* gum, is particularly effective in this invention and its use as a/the polyglucomannan forms a specific aspect of the invention. *Konjak*, *Amorphophallus konjak*, also known as Konjac and Devil's Tongue, is a tuber plant grown in Asia as a food plant. The carbohydrate components of the tuber include *Konjak* polyglucomannan Naturally occurring *Konjak* polyglucomannan typically has a molecular weight of about $1.10^6$ to about $2.10^6$, but processing e.g. refining and milling, can reduce the molecular weight.

The emulsions of the invention have aqueous continuous phases and in making the emulsions the polysaccharides will usually be dispersed in water. The particle size of the polysaccharides, especially the polyglucomannan, can be important in achieving good dispersion in water, especially relatively cool, particularly cold (ambient temperature) water. *Konjak* polyglucomannan is readily dispersible in hot water at concentrations of 0.001 to 0.5% by weight. However, as typically derived from the tuber, *Konjak* polyglucomannan has a relatively large particle size typically having an average particle size of from about 100 to about 2000 $\mu$m. Material with this particle size tends to have relatively poor cold water dispersibility. Milling to lower particle size e.g. from about 50 to about 200 $\mu$m, can make the product much more readily cold water dispersible. Cold water dispersibility of Xanthan polymers in the form of their commercially available powders is not usually a problem.

As indicated above Xanthan polymers typically have molecular weights of the order of $2.10^6$. Significant reduction of this molecular weight is generally undesirable as this has an adverse effect on the properties of the Xanthan. For the polyglucomannans, particularly *Konjak* polyglucomannan, the molecular weight is less important provided that the product is not otherwise substantially chemically degraded. Materials with molecular weights as low as about $2.10^5$, corresponding to notional fragments of about 1/10 of the original polymer, can be effective in the present invention.

The combination of Xanthan and *Konjak* polysaccharides as the emulsion stabiliser is particularly advantageous and forms a specific aspect of the invention, including the various embodiments described and the invention accordingly includes a personal care or cosmetic oil In water emulsion which includes as an emulsifier stabiliser system an emulsifier for the oil and a polysaccharide combination of a Xanthan polysaccharide and a *Konjak* polyglucomannan polysaccharide.

Xanthan and polyglucomannan polysaccharides are believed to form complexes which give synergistic thermoreversible gels in aqueous systems (see for example "Biopolymer Mixtures" published by Nottingham University Press [1995], Chapter 14 by V J Morris), but the detailed structure of these complexes have not been definitively established. Similarly other polysaccharide combinations can also give aqueous gels. These properties do not account for the emulsion stabilising effect obtained in this invention, because stable emulsions can be obtained at comparatively low viscosities. This result is remarkable as using other gelling materials such as Tara, Carageenan, Locust bean, Guar and Alginate gums, alone or in combination with Xanthan, we have not been able to combine good emulsion stability with acceptable skin feel and body properties. The results we have obtained suggest that these other gelling materials provide emulsion stabilisation because they provide increased emulsion viscosity. Similarly, the literature reports that in aqueous solution Xanthan typically exists as molecular aggregations sometimes referred to as a dimer. This may explain why we have found that the stabilising effect of the Xanthan/polyglucomannan can be promoted by heating and/or vigorously mixing an aqueous dispersion of the Xanthan and polyglucomannan before emulsifying the oil in the aqueous system (see below). In any event we do not know why we have been able to make very stable emulsions according to the present invention and do not wish to be restricted to any particular "theory" to explain it.

We have found that an improvement in stabilising emulsions can be obtained at weight ratios of Xanthan to polyglucomannan, particularly *Konjak* polyglucomannan, from about 1:10 to about 10:1, particularly about 4:1 to about 1:4, with more desirable results in the range about 2:1 to about 1:2 and especially about 1:1. This remains the case even when lower molecular weight polyglucomannan is used and the relative constancy of this ratio suggests that when lower molecular weight polyglucomannan is used, the combination formed may include several polyglucomannan molecules for each molecule of Xanthan.

The amount of the polysaccharide stabiliser used will generally be enough to provide an improvement in emulsion stability and more desirably to give adequate emulsion stability. However, the inclusion of amounts of polysaccharide stabiliser significantly in excess of that needed to achieve emulsion stability is undesirable as this can give substantial thickening of the emulsion. Aqueous systems, including emulsions thickened with Xanthan, polyglucomannan or the polysaccharide stabiliser generally have a shear thinning pseudoplastic Theological profile but give slimy and/or stringy products with poor body and/or skin feel that is undesirable in personal care products. These properties represent a significant disincentive to the use of these polysaccharides alone or in combination in personal care and cosmetic emulsions.

The use of even very low concentrations of polysaccharide stabiliser e.g. as low as about 0.01% by weight of the emulsion, can give useful improvements in emulsion stability. In practice, the amount of the polysaccharide stabiliser used will be chosen to give emulsions with extended stability and will generally be at least about 0.02% by weight of the emulsion. The maximum concentration generally used depends on the emulsion system, but is typically about 0.5% by weight of the emulsion. Thus, suitable general concentration ranges are from about 0.02% to about 0.5%, more usually from 0.025 to about 0.25%, particularly up to about 0.2% and especially from 0.025 to 0.15%, by weight of the emulsion. Relatively high concentrations in these ranges may be used e.g. where particularly difficult emulsions are being made including those using very hydrophobic oils, or and especially in cream formulations, or where electrolyte may be present (see below), even though the rheology may not be ideal.

The emulsions made and stabilised according to the invention can have exceptionally high stability even at elevated temperatures e.g. up to about 50° C. However, the polysaccharide combinations are sensitive to ionic materials which act to destabilise the emulsions. We believe that the presence of ionic materials destabilises the Xanthan/polyglucomannan combination so that it is less available to provide effective emulsion stabilisation. For this reason, ionic materials e.g. acids, bases: and salts including neutral salts, such as organic or inorganic salts, are desirably present only at low concentrations in the emulsions of this invention, or are absent. Generally the concentration of ionic materials will not greater than about 0.05 molar, desirably not more than about 0.02 molar and particularly not more than about 0.01 molar. Similarly, ionic surfactants, including emulsifiers, including anionic, cationic and zwiterionic surfactants are desirably not present at significant concentrations in the emulsions of the invention. Amphoteric surfactants can be used, but usually only under conditions where they do not support charged species and, as this tends to be an environment where amphoteric surfactants are not particularly effective, they are not usually desirably included.

Accordingly, the emulsifier used in the invention is desirably one or more non-ionic emulsifier(s). Suitable emulsifiers include conventional non-ionic oil-in-water emulsifier surfactants such as alkoxylate emulsifiers and surfactants that can be derived from natural materials such as fatty acid esters, ethers, hemi-acetals or acetals of polyhydroxylic compounds or a fatty acid amide which is N-substituted with the residue of a polyhydroxylic compound. The specific nature of the emulsifier surfactant used in any particular instance depends on the type of emulsion being made, particularly whether fatty amphiphilic thickeners are being used, the degree of stability required, the nature of the oil being emulsified and the total desired level of emulsifier/stabiliser system.

The term alkoxylate emulsifier is used to refer to surfactants in which a hydrophobe, usually a hydrocarbyl group, is connected through the residue of a linking group having a reactive hydrogen atom to an oligomeric or polymeric chain of alkylene oxide residues. The hydrocarbyl group is typically a chain, commonly an alkyl chain, containing from 8 to 24, particularly 12 to 22, and usually 14 to 20 carbon atoms. The linking group can be an oxygen atom (hydroxyl group residue); a carboxyl group (fatty acid or ester residue); an amino group (amine group residue); or a carboxyamido (carboxylic amide residue). The alkylene oxide residues are typically residues of ethylene oxide ($C_2H_4O$) or propylene oxide ($C_3H_6O$) or combinations of ethylene and propylene oxide residues. When combinations are used the proportion of ethylene oxide residues will usually be at least about 50 mole % and more usually at least 75 mole %, the remainder being propylene oxide residues. Particularly and desirably, substantially all the residues are ethylene oxide residues. The number of alkylene residues in the emulsifier molecule is desirably from 2 to about 200. At least theoretically, alkyl phenyl ethoxylates could be used, but these are generally not now desired in personal care and cosmetic products for other reasons and are thus not usually used in this invention.

The number of alkylene oxide residues is usually from 2 to 200 per mole of alkoxylate emulsifiers and will vary depending on the balance between hydrophilic and hydrophobic properties desired in the emulsifier (see below). Examples of suitable alkoxylate emulsifiers include alcohol alkoxylates, of the formula (Ia): $R^1$—O-(AO)$_n$—H; a fatty acid alkoxylate of the formula (Ib): $R^1$—COO-(AO)$_n$—$R^2$ (plus co-products); a fatty amine alkoxylate of the formula (Ic): $R^1$—$NR^3$-(AO)$_n$—H; or a fatty amide alkoxylate of the formula (Id); $R^1$—$NR^3$-(AO)$_n$—H, where each $R^1$ is independently a $C_8$ to $C_{24}$, particularly $C_{12}$ to $_{22}$, hydrocarbyl, particularly alkyl group; $R^2$ is a hydrogen atom or a $C_1$ to $C_6$ alkyl group; and each $R^3$ is independently a $C_1$ to $C_6$ alkyl group or a group (AO)$_n$—H; each AO is independently an ethylene oxide or propylene oxide group; and the total of the indices n in the molecule is from 2 to 200.

Using alkoxylate emulsifiers, the invention includes a personal care or cosmetic oil in water emulsion, particularly an emulsion having a low shear viscosity of up to about 10000 mPa.s, which includes as an emulsifier stabiliser system an alkoxylate emulsifier for the oil in an amount of from about 0.02 to about 1.5% by weight of the emulsion and a polysaccharide stabiliser in an amount of from about 0.02 to about 0.25% by weight of the emulsion. Further, using high HLB (see also below) alkoxylate emulsifiers, the emulsifier stabiliser system of the invention can be effective at very low levels, and is particularly applicable to low viscosity systems (if only because some materials used to increase emulsion viscosity may require the presence of further emulsifier to disperse them), and accordingly the invention includes a personal care or cosmetic oil in water emulsion, particularly an emulsion having a low shear viscosity of up to about 10000 mPa.s, which Includes as an emulsifier stabiliser system an alkoxylate emulsifier for the oil in an amount of from about 0.02 to about 0.25% by weight of the emulsion and a polysaccharide stabiliser in an amount of from about 0.02 to about 0.25% by weight of the emulsion.

Creams can be made using alkoxylate emulsifiers, but generally the amount of emulsifier will be higher than the minimum to stabilise a milk emulsion. The invention thus includes a personal care or cosmetic oil in water cream emulsion having a low shear viscosity of more than about 20000 mPa.s, which includes as an emulsifier stabiliser system an emulsifier, including an alkoxylate emulsifier, for the oil in an amount of from about 0.25 to about 1.5%, particularly from about 0.5 to about 1%, by weight of the emulsion and a polysaccharide stabiliser in an amount of from about 0.02 to about 0.5%, particularly from about 0.05 to about 0.25, by weight of the emulsion the emulsion further including thickener components.

The emulsifier stabiliser system of the invention is flexible in that emulsifiers that are not derivatives of alkylene oxides can be used. This opens up the possibility of using emulsifier stabiliser systems which are derived entirely from biological, particularly vegetable, source materials. This possibility may be attractive to formulators of personal care products. In this aspect, the invention, therefore, further includes a personal care or cosmetic oil in water emulsion which includes as an emulsifier stabiliser system an emulsifier for the oil, which is a fatty acid ester, ether, hemi-acetal or acetal of a polyhydroxylic compound, or a fatty acid amide which is N-substituted with the residue of a polyhydroxylic compound, especially a saccharide fatty acid ester, and a polysaccharide stabiliser. Sugar (saccharide) esters can be used with advantage in this invention as they can provide very stable emulsions which can entirely avoid using products manufactured using alkylene oxides and can enable the use of emulsifier/stabiliser systems which are derived entirely from "natural" biological source, particularly vegetable source materials.

Particularly useful esters of polyhydroxylic compounds include saccharide esters particularly mono-esters of fatty acids and a sugar, especially sucrose, fructose and/or glucose. Commercially available sugar esters are usually mixtures containing mono-ester, higher esters and sometimes free starting material (sugar). In this invention it is desirable to use sugar esters having a relatively high proportion of mono-ester. Typically the sugar ester used will have a content of mono-ester of at least 50% more usually at least 60% and desirably at least 65%. The proportion may be higher e.g. 70%, 80% or even higher, although products with very high proportions of mono-ester are significantly more expensive and we have not found any particular advantage in using products with more than about 75% mono-ester. Sucrose esters are particularly useful in the invention. Such sugar esters are relatively hydrophilic emulsifiers and less hydrophilic variants can be used in which hydroxyl groups (usually only one) on the saccharide residue are etherified (or acetalated) typically with a $C_1$ to $C_4$ alkyl group e.g. a methyl group. Desirable sugar esters may be of the formula (IIa): $R^1$—COO-$(G)_a$, where $R^1$ is as defined above for alkoxylate emulsifiers; each G is independently a saccharide residue, particularly a glucose, mannose or fructose residue and a is from 1 to about 5, particularly about 2, especially the residue $(G)_a$ is the residue of sucrose or glucose.

Other esters of polyhydroxylic compounds include esters of fatty acids, particularly fatty acids having from 8 to 24, usually 12 to 22, more usually 16 to 20 carbon atoms, and polyols particularly glycerol, or a polyglycerol, or an anhydro-saccharide such as sorbitan. Generally, these materials are desirably also mainly used as the mono-ester. Examples include glycerol mono-laurate, triglycerol mono-stearate and among relatively more hydrophobic emulsifiers glycerol mono-stearate and sorbitan mono-oleate, stearate or laurate. Suitable such esters may be of the formula (IIb): $R^1$—COO—$R^4$, where $R^1$ is as defined above for alkoxylate emulsifiers; and $R^4$ is a polyhydroxyl hydrocarbyl group, particularly an alkyl group or alkyl ether group containing from 3 to 10 carbon atoms and 2 to 6 hydroxyl groups. Such materials may be used on combination with other e.g. ester emulsifiers as in the blend of (nominally) polyglyceryl stearate and methyl glucoside stearate sold under the trade designation Tego Care 450 by Goldschmidt.

Yet further ester emulsifiers include fatty acid esters of hydroxycarboxylic acids, in particular the products of trans esterification between fatty glycerides, especially mono- and di-glycerides, and polyhydroxy-carboxylic acids. These products are usually described as esters, but are typically mixtures of the starting materials and the trans-esterification products, particularly where the fatty acid residues are esterified to hydroxyl groups on the hydroxycarboxylic acids. In these products, the fatty acid typically has from 8 to 24, usually 12 to 22, more usually 16 to 20 carbon atoms and the hydroxycarboxylic acid is desirably citric acid.

Another type of emulsifier derived from sugars are saccharide hydrocarbyl ethers, hemi-acetals or acetals, commonly known as hydrocarbyl, particularly alkyl, polysaccharides (more properly oligo saccharides), and in particular materials of the formula (IIc): $R^1$—O-$(G)_a$, where $R^1$ is as defined above for alkoxylate emulsifiers; each G is independently a saccharide residue, particularly a glucose residue and a is from 1 to about 5, particularly from about 1.3 to about 2.5.

A further emulsifier type is of N-substituted fatty acid amides in which the N-substituent is the residue of a polyhydroxylic compound, which is commonly a saccharide residue such as a glucosyl group. This type of emulsifier includes materials of the formula (IId): $R^1$—CO—$NR^5R^6$, where $R^1$ is as defined above for alkoxylate emulsifiers; $R^5$ is a hydrogen atom, a $C_1$ to $C_6$ alkyl group or a group of the formula $R^6$; and $R^6$ is a polyhydroxyl hydrocarbyl group, particularly a group containing from 3 to 10 carbon atoms and 2 to 6 hydroxyl groups and is typically a glucosyl residue.

In this aspect the invention includes low viscosity milk emulsions and higher viscosity cream emulsions. Specifically, the invention includes a personal care or cosmetic oil in water emulsion milk having a viscosity of up to about 10000 mPa.s, which includes as an emulsifier stabiliser system an emulsifier for the oil, which is a fatty acid ester, ether, hemi-acetal or acetal of a polyhydroxylic compound, or a fatty acid amide which is N-substituted with the residue of a polyhydroxylic compound, in an amount of from about 0.5 to about 1.5% by weight of the emulsion and a polysaccharide stabiliser in an amount of from about 0.02 to about 0.5% by weight of the emulsion. The invention further specifically includes a personal care or cosmetic oil in water cream emulsion having a viscosity of more than about 20000 mPa.s, which includes as an emulsifier stabiliser system an emulsifier for the oil which is a fatty acid ester, ether, hemi- acetal or acetal of a polyhydroxylic compound or a fatty acid amide which is N-substituted with the residue of a polyhydroxylic compound, in an amount of from about 0.5 to about 1.5% by weight of the emulsion and a polysaccharide stabiliser in an amount of from about 0.02 to about 0.5% by weight of the emulsion, the emulsion further including thickener components.

It can be useful to use a combination of different types of emulsifier and in particular to combine hydrophilic emulsifiers i.e. having a high Hydrophile Lipophile Balance (HLB) e.g. more than about 12, and hydrophobic emulsifiers i.e. having a low HLB e.g. less than about 8, in making the emulsions of the invention. Relatively hydrophilic emulsifiers include alkoxylate emulsifiers with an average of from about 10 to about 100 alkylene oxide, particularly ethylene oxide residues; and non-alkoxylate emulsifiers including sugar mono-esters and polyglycerol mono-esters, hydrocarbyl, especially alkyl, polysaccharides; fatty acid glycerol esters where the fatty acid has 8 to 12 carbon atoms such as glycerol mono-laurate and fatty acid N-sugar amides such as glucamides. Relatively hydrophilic emulsifiers include alkoxylate emulsifiers with an average of from 2 to about 10 alkylene oxide, particularly ethylene oxide residues; glycerol esters where the fatty acid has 14 to 24 carbon atoms such as glycerol mono-stearate, -oleate, or -laurate; and anhydrosaccharide fatty esters such as sorbitan mono-stearate, -oleate, or -laurate.

The amount of emulsifier used is typically from about 0.02 to about 1.5%, more usually from about 0.025 to about 1.2%, particularly from about 0.025 to about 1%, by weight of the emulsion. Where hydrophilic alkoxylate emulsifiers, especially those with HLB greater than about 12, are used it is possible to obtain satisfactory emulsions with very low levels of emulsifier for example from as little as about 0.04 to about 0.1% by weight of the emulsion, and this forms a particular feature of the invention. Higher amounts of such emulsifiers can be used e.g. in the overall range about 0.04 to about 0.8%, particularly about 0.1 to about 0.6%, by weight. Where less hydrophilic alkoxylate emulsifiers are used as the primary emulsifier, the concentration used will typically be higher e.g. in the range from about 0.1 to about 1.5%, more usually from about 0.2 to about 1.2, particularly from about 0.5 to about 1%, by weight of the emulsion. Similarly where non-alkoxylate emulsifiers such as fatty acid esters, ethers, hemi-acetals or acetals of polyhydroxylic compounds, or fatty acid N-(polyhydroxyl residue substituted) amides, are used as the main emulsifier, the amount used will typically be from about 0.2 to about 1 2, more usually from about 0.3 to about 1%, particularly from about 0 4 to 0.8%, by weight of the emulsion.

When a combination of hydrophilic (high HLB e.g. more than about 10) and hydrophobic (low HLB e.g. less than about 8) emulsifiers is used, the amount of hydrophilic emulsifier will typically be in the ranges set out above and the amount of relatively hydrophobic emulsifier will typically be from 0.1 to 1%, particularly from about 0.2 to about 0.8%. In such combinations, the total amount of emulsifier is typically from about 0.5 to 1.5%, particularly from 0.1 to 1%, by weight of the emulsion. The use of combinations of hydrophilic and hydrophobic emulsifier (sometimes called a co-emulsifier) is particularly useful when the oil phase is highly hydrophobic (non-polar) or when the emulsion is thickened by the inclusion of fatty amphiphiles (see below). In such combinations the overall HLB of the emulsifier system will typically be from about 8 to about 12.

We have found that the inclusion of more emulsifier, particularly of a relatively hydrophilic emulsifier, than is needed to provide a suitably small emulsion droplet size, may have a detrimental effect on emulsion stability. Excess of relatively more hydrophobic emulsifiers seems less detrimental to stability and may contribute to a desired emulsion rheology (relatively hydrophobic emulsifiers are chemically fairly similar to fatty amphiphiles such as can be used as thickeners—see below).

It is generally technically possible to freely combine non-ionic emulsifiers of the alkoxylate and non-alkoxylate types described above. Such combinations may be attractive where the emulsifier system includes a hydrophilic alkoxylate emulsifier e.g. using a low HLB non-alkoxylate emulsifier in combination. However, hydrophilic non-alkoxylate emulsifiers, especially sugar mono-ester emulsifiers, are more expensive than typical alkoxylate emulsifiers and will usually be used only when it is desired to have an emulsifier stabiliser system which includes no derivatives of alkylene oxides.

The oil phase used will typically mainly be an emollient oil of the type widely used in personal care or cosmetic products. The emollient can and usually will be an oily material which is liquid at ambient temperature. Alternatively it can be solid at ambient temperature, in which case in bulk it will usually be a waxy solid, provided it is liquid at an elevated temperature at which it can be included in and emulsified in the composition. As is described below manufacture of the composition usually uses temperatures up to about 100° C. usually about 80° C. so such solid emollients will have melting temperatures of less than 100° C. and usually less than 70° C.

Suitable normally liquid emollient oils include non-polar oils, for example mineral or paraffin, especially isoparaffin, oils, such as that sold by ICI Surfactants as Arlamol HD; or medium polarity oils, for example vegetable glyceride oils such as jojoba oil, animal glyceride oils, such as that sold by ICI Surfactants as Arlamol M812 (caprilic/capric triglyceride), synthetic oils, for example synthetic ester oils, such isopropyl palmitate and those sold by ICI Surfactants as Arlamol IPM and Arlamol DOA, ether oils, particularly of two fatty e.g. C8 to C18 alkyl residues, such as that sold by Henkel as Eutanol G (octyl dodecanol), or silicone oils, such as dimethicone oil such as those sold by Dow Corning as DC200, cyclomethicone oil, or silicones having polyoxyalkylene side chains to improve their hydrophilicity; or highly polar oils including alkoxylate emollients for example fatty alcohol propoxylates such as that sold by ICI Surfactants as Arlamol E (stearyl alcohol 15-propoxylate). Suitable emollient materials that can be solid at ambient temperature but liquid at temperatures typically used to make the compositions of this invention include jojoba wax, tallow and coconut wax/oil. When non-polar oils are used it may be desirable to use relatively high concentrations of emulsifier, particularly high HLB emulsifier, in order to achieve suitably satisfactory emulsification, particularly to obtain small oil droplets.

Mixtures of emollients can and often will be used and in some cases solid emollients may dissolve wholly or partly in liquid emollients or in combination the freezing point of the mixture is suitably low. Where the emollient composition is a solid at ambient temperature, the resulting dispersion may technically not be an emulsion (although in most cases the precise phase of the oily disperse phase cannot readily be determined) but such dispersions behave as if they were true emulsions and the term emulsion is used herein to include such compositions.

The concentration of the oil phase may vary widely. Generally the oil phase concentration will be at least about 1%, and more usually at least about 5%, by weight and in products as used the oil concentration can be as high as about 30%. Certainly we have readily obtained stable emulsions at oil phase content of upwards of 20% by weight. Even higher concentrations are possible, we have made emulsions at up to 80% by weight of oil, and these concentrated emulsions may be used as pre-manufactured concentrates for dilution with other components to make product emulsions.

The polysaccharide stabilisers used in this invention can be used in other contexts as thickeners, but when used as thickeners, although they seem to provide shear thinning properties we have found that they give emulsion products which have a cosmetically poor body and skin feel commonly described as "stringy" and/or "slimy" materials. These properties are undesirable in cosmetics and personal care products, so the inclusion of excess polysaccharide stabiliser or the individual polysaccharides is not usually satisfactory for thickening emulsions e.g. to form creams, for personal care or cosmetic products and is not generally used in this invention.

More desirable ways of rheology modification to make higher viscosity products include the use of materials which build up a network of particles in the continuous water phase. Particularly suitable materials include fatty amphiphiles such as fatty alcohols, fatty acids and waxes. Suitable materials include fatty alcohols, particularly $C_8$ to $C_{24}$, especially $C_{14}$ to $C_{20}$ fatty alcohols such as stearyl alcohol, e.g. as commercial cetearyl alcohol (a mixture mainly of cetyl and stearyl alcohols); fatty acids, particularly $C_8$ to $C_{24}$, especially $C_{14}$ to $C_{20}$ fatty acids such as stearic acid; and waxes such as microcrystalline wax such as that sold by Fuller as Lunacera M. The technical boundary between hydrophobic surfactants and fatty amphiphiles is not always clear and the presence of low HLB emulsifiers may contribute to thickening by fatty amphiphiles. Fatty amphiphiles used as thickeners in this invention will commonly be used as mixtures of materials e.g. from a natural source, a distillation cut during manufacture or deliberately blended to give a mixture. The precise mechanism by which fatty amphiphiles contribute to thickening is not fully understood, but they appears to contribute to structure in the aqueous phase.

Other thickeners that can be used include polymeric thickeners such as starches, particularly modified starches, for example modified potato starch, such as that sold by National Starch as Structure Solanace, and modified maize starch such as that sold by National Starch as Structure Zea (hydroxypropyl distarch phosphate); cellulose thickeners such as carboxyalkylcellulose for example carboxymethyl cellulose such as that sold by Hercules as Natrosol 250HHR (hydroxyethyl cellulose), or that sold by FMC as Avicel RC-591 (a mixture of sodium carboxymethylcellulose and microcrystalline cellulose); polysaccharide gums such as Tara, Carrageenan, Guar, Locust Bean, Xanthan and *Konjak* gums (although with the amounts used may need to be limited to avoid undesirable skin feel and body properties in the emulsion products) and modified gums such as guar hydroxypropyl ether; and synthetic thickeners such as polyacrylic thickeners such as carbomers including the Carbopol resins from Goodrich (although care may be needed with these as they are ionic although they are by weight very effective thickeners and can be used without necessarily making the emulsions unstable).

An important advantage of the invention is that thickened emulsions can be made in which the emulsion is thickened substantially independently of emulsion stabilisation. This affords product formulators much greater freedom in designing cream systems having a desired rheology as compared with the use of thickeners to stabilise emulsions, because the rheology is not restricted by that used in stabilising the emulsion. For reasons which are not clear, using some thickeners, an additive and possibly synergistic effect in thickening emulsions of the invention using the polysaccharide stabiliser has been noted.

When the oil phase components include fatty amphiphiles e.g. included as thickeners, higher concentrations of emulsifier, particularly high HLB emulsifier, and/or the use of combinations of hydrophilic and hydrophobic emulsifiers may need to be used in order to adequately disperse the fatty amphiphile. However, we have achieved satisfactory results using total emulsifier levels not exceeding about 1.5% and usually not more than about 1.2% and particularly desirably so that the total emulsifier polysaccharide stabiliser concentration is not more than about 1%.

The composition of the emulsions of the invention, with regard to the main components, typically fall within the ranges in the tables below.

| | amount (wt %) | | | |
|---|---|---|---|---|
| | using alkoxide emulsifiers | | using non-alkoxide emulsifiers | |
| Material | broad | preferred | broad | preferred |
| oil | 1 to 80 | 5 to 30 | 1 to 80 | 5 to 30 |
| total emulsifier | 0.02 to 1.5 | 0.025 to 1.2 | 0.1 to 1.5 | 0.5 to 1.2 |
| high HLB emulsifier | 0.02 to 1.2 | 0.025 to 1.0 | 0.2 to 1.2 | 0.4 to 1.0 |
| *low HLB emulsifier | 0.1 to 1.2 | 0.5 to 1.0 | 0.1 to 1.2 | 0.2 to 1.0 |
| polysaccharide stabiliser | 0.02 to 0.5 | 0.025 to 0.25 | 0.02 to 0.5 | 0.025 to 0.25 |
| thickener (when used) | 0.1 to 10 | 0.25 to 7 | 0.1 to 10 | 0.25 to 7 |
| water** | to 100 | to 100 | to 100 | to 100 |

*used in combination with a high HLB emulsifier
**after allowing for minor components and additives The emulsions and formulations of this invention are typically near acid/base neutrality—their sensitivity to ionic materials is mentioned above. Moderate deviation from neutrality is possible without losing the stability advantages of the invention. Desirably the pH is from 4 to 9, more desirably 4.5 to 8 and particularly usefully from 6 to 8.

Many other components may be included in the emulsion compositions of the invention to make personal care or cosmetic formulations. These components can be oil soluble, water soluble or non-soluble. Among water soluble components, care may be needed with materials that provide electrolyte to the composition or cause marked shifts in pH (see above). Examples of such materials include:

preservatives such as those based on parabens (alkyl esters of 4-hydroxybenzoic acid), phenoxyethanol, substituted ureas and hydantoin derivatives e.g. those sold commercially under the trade names Germaben II Nipaguard BPX and Nipaguard DMDMH, when used usually in a concentration of from 0.5 to 2% by weight of the emulsion;

perfumes, when used typically at a concentration of from 0.1 to 10% more usually up to about 5% and particularly up to about 2% by weight of the emulsion;

humectants or solvents such as alcohols, polyols such as glycerol and polyethylene glycols, when used typically at a concentration of from 1 to 10% by weight of the emulsion;

sunfilter or sunscreen materials including chemical sunscreens and physical sunscreens including those based on titanium dioxide or zinc oxide; when used typically at from 0.1% to 5% by weight of the emulsion (but noting that physical sunscreen materials are often dispersed using acrylic polyanionic polymers that may tend to destabilise the emulsions because they supply electrolyte);

alpha hydroxy acids such as glycolic, citric, lactic, malic, tartaric acids and their esters;

self-tanning agents such as dihydroxyacetone;

antimicrobial, particularly anti-acne components such as salicylic acid;

Vitamins and their precursors including:
 a) Vitamin A e.g. as retinyl palmitate and other tretinoin precursor molecules,
 b) Vitamin B e.g. as panthenol and its derivatives,
 c) Vitamin C e.g. as ascorbic acid and its derivatives,
 d) Vitamin E e.g. as tocopheryl acetate,
 e) Vitamin F e.g. as polyunsaturated fatty acid esters such as gamma-linolenic acid esters;

skin care agents such as ceramides either as natural materials or functional mimics of natural ceramides;

phospholipids;

vesicle-containing formulations;

germanium-containing compounds for example that sold by ICI Surfactants as Arlamol GEO;

botanical extracts with beneficial skin care properties;

skin whiteners such as hydroquinone, kojic acid, arbutin and similar materials;

skin repair compounds actives such as Allantoin and similar series;

caffeine and similar compounds;

cooling additives such as menthol or camphor;

insect repellents such as N,N-diethyl-3-methylbenzamide (DEET) and citrus or eucalyptus oils;

essential oils; and pigments, including microfine pigments, particularly oxides and silicates, e.g. iron oxide, particularly coated iron oxides, and/or titanium dioxide, and ceramic materials such as boron nitride, or other solid components, such as are used in make up and cosmetics, to give suspoemulsions, typically used in an amount of from about 1 to about 15%, but usually at least about 5% and particularly about 10%.

The emulsions of the invention can be formulated either as simple emulsions which may be thickened as is described above or they can be formulated in more complex systems such as suspoemulsions or multiple emulsions. Suspoemulsions include a liquid dispersed phase and a solid dispersed phase. As is mentioned above, the solid can be a pigment e.g. titanium dioxide and/or coloured iron oxides; or a physical sunscreen of a metal oxide such as titanium and/or aluminium and/or zinc oxides, in which case the particles of oxide may be fine enough that they do not scatter visible light (although they will be selected to scatter UV light). The invention therefore includes a suspoemulsion which is an emulsion of the invention additionally including a dispersed solid material, particularly a pigment.

Other forms of more complex system include multiple emulsions in which the dispersed phase of an emulsion has within its droplets a dispersion of droplets of another liquid. There are thus two emulsions a primary or outer emulsion and a secondary or inner emulsion and the phases can be described as primary or outer and secondary or inner external and internal phases. There are thus two internal phases which are commonly referred to as the outer or primary internal phase and the inner or secondary internal phase and two external phases commonly referred to as the outer or primary external phase and the inner or secondary external phase. There are two basic types of multiple emulsion water in oil in water and oil in water in oil. Both types of multiple emulsion can be made using the emulsification stabilisation system of this invention. The invention thus further includes a water in oil in water multiple emulsion in which the primary oil in water emulsion is an emulsion of the invention and an oil in water in oil in which the secondary or inner emulsion is an emulsion of the invention. The secondary internal phase of multiple emulsions can be used to deliver materials which are sensitive to environmental conditions or to materials in the primary external phase.

The emulsions of the invention can be used, as described above, as cosmetic or personal care products in themselves or can be fabricated into such products. In particular they can be used to impregnate tissues particularly paper tissues e.g. to provide cleansing wipes. In this application the emulsion will typically contain a relatively low proportion of oil phase typically from 3 to 15% more usually about 5% by weight of the emulsion. The amount of emulsion impregnated into tissues will depend on the desired properties in the end product, but will typically be from 10 to 100 $g.m^{-2}$ of tissue. The tissues will typically have a basis weight of from 30 to 100 $g.m^{-2}$. The invention thus includes a cleansing tissue which is impregnated with an emulsion of the invention. Another use for the emulsions of the invention is to remove make up or other cosmetics. We have found that emulsions of the invention are effective in this use and can be broadly as efficient as the neat oil in removing oily make up e.g. mascara, particularly "waterproof mascara". This is a surprising result as the emulsions in this use typically do not contain very high proportions of oil, typical amounts would be from 25 to 50, more usually from 15 to 30% by weight of the emulsion.

The emulsions of the invention can be made by generally conventional emulsification and mixing methods. Typical methods include direct emulsification by first dispersing the emulsifier(s) and polysaccharide stabiliser (either added as separate components or together) in the aqueous phase and then mixing in and emulsifying the oil in the aqueous continuous phase. To ensure formation of the polysaccharide emulsion stabiliser combination it is desirable to either heat she aqueous phase containing the Xanthan and polyglucomannan usually above about 60° C. e.g. to about 80 to 85° C., or to subject the aqueous phase to high intensity mixing at lower e.g. about ambient temperature. Vigorous mixing and the use of moderately elevated temperatures can be combined if desired. The heating and/or high intensity mixing can be carried out before, during or after addition of the oil phase.

The emulsions can also be made by inverse emulsification methods, particularly where low HLB emulsifiers are used (typically in combination with high HLB emulsifiers). In such methods, the emulsifier components, usually including the polysaccharide stabiliser, (either added as separate components or together) in the oil phase and aqueous phase is then added and mixed into the oil phase to form a water in oil emulsion. Aqueous phase addition is continued until the system inverts to for an oil in water emulsion. Plainly a substantial amount of aqueous phase will generally be needed to effect inversion and so this method is not likely to be used for high oil phase content emulsions. As described above, to ensure formation of the polysaccharide emulsion stabiliser combination it is desirable to either heat the Xanthan and polyglucomannan in or in contact with the aqueous phase usually above about 60° C. e.g. to about 80 to 85° C., or to subject them to high intensity mixing at lower e.g. about ambient temperature. Vigorous mixing and the use of moderately elevated temperatures can be combined if desired. The heating and/or high intensity mixing can be carried out during or after addition of the aqueous phase and before during or after inversion.

Generally we have found that the hot dispersion methods give emulsions that are more stable than those made by the cold dispersion methods, but cold dispersion is very convenient, particularly for formulators and can give good results. Of course where components needing processing at higher temperatures are used e.g. relatively high melting point waxes, hot dispersion may be convenient for this reason. After making the emulsions the disperse phase concentration can readily adjusted by addition of further continuous phase material, usually with gentle mixing. In the context of making the emulsions, vigorous or high intensity mixing refers to mixing at shear rates typically used in emulsification and will usually be at a shear rate of at least about $10^4$ sec$^{-1}$.

When relatively high viscosity emulsions are made, water soluble or dispersible thickener components can be included in the aqueous phase suitably after dispersion of the emulsifier and emulsion stabiliser and oil soluble or dispersible thickening components can be dispersed or dissolved in the oil phase and incorporated into the emulsion with the oil.

The invention accordingly includes a method of making an emulsion which includes the steps of 1 dispersing the emulsifier(s) and polysaccharide stabiliser in the aqueous phase, 2 optionally including thickener components in the aqueous phase; and 3 mixing in and emulsifying the oil in the aqueous continuous phase, and in which the aqueous dispersion of the emulsifier(s) and polysaccharide stabiliser is heated to a temperature of at least about 60° C. and/or is vigorously mixed before or during emulsification of the oil.

The emulsions of the invention can be used in a wide variety of personal care and cosmetic products and the invention includes such products and the use of the emulsions of the invention in such products as specific aspects of the invention. The emulsions of the present invention can be incorporated into both milk and cream products. Examples of such products include cleansing milks and creams; skin moisturising milks and creams; cosmetic remover milks and creams; and sunscreens, usually in milk or sprayable emulsion milk forms.

The emulsifier and emulsion stabiliser components used in the invention can be blended to provide a dry formulation that can be dispersed in water and readily then made into emulsions and as noted previously, this forms an aspect of the invention. Typically these dry formulations include the solid components including the emulsifier and polysaccharide stabiliser. For such formulations it-is useful to use both high HLB and low HLB emulsifiers and optionally to include materials such as milling aids for example sugars, particularly glucose and/or sucrose, which provide relatively hard materials to aid milling and grinding if needed and also act as readily soluble materials aiding subsequent aqueous dispersion of the formulations. Such formulations can be made by dry blending Xanthan and polyglucomannan polysaccharides, emulsifiers and optionally sugar, if desired consolidating the blend e.g. by extrusion, to form pellets and then milling the pellets to a desired particle size.

Desirably the materials are processed at a temperature, typically from 50° C. to 100° C., sufficient that one or more of the components typically one or more of the emulsifiers are at least partly melted and can so coat and/or bind the powder components, typically including the polysaccharides. The emulsifier components may desirably be completely melted and the polysaccharides mixed into this melt. This mixing can be carried out using an extruder of a batch mixer and the product can be solidified into flakes or pellets which can, if necessary, be subsequently milled to make more finely divided particles.

The composition of the dry formulation with regard to the main components, typically fall within the ranges in the table below.

| Material | (parts by wt) | |
|---|---|---|
| | broad | preferred |
| Xanthan | 2 to 10 | 3 to 8 |
| polyglucomannan | 2 to 10 | 3 to 8 |
| ratio Xanthan:polyglucomannan | 1:4 to 4:1 | 1:2 to 2:1 |
| total emulsifier | 25 to 80 | 30 to 70 |
| high HLB emulsifier | 30 to 75 | 40 to 70 |
| *low HLB emulsifier | 5 to 40 | 10 to 30 |
| milling aid (optional) | 2 to 10 | 3 to 8 |

*when used in combination

Particularly where the dry formulation is intended to be cold dispersible, it (the dry blended product) is desirably a powder having a mean particle size of from about 100 to about 500 μm. To make handling more straightforward e.g. to reduce the risk of powder combustion, the powder desirably contains little or no material having a much lower particle size. In particular, the proportion of particles of size lower than 50 μm is less than 10% (by weight), desirably less than 2%, particularly less than 1%. If cold dispersibility is not an important requirement, the physical form of the dry formulation may be even less finely divided e.g. pastilles, pellets and/or flakes. In such forms the average particle sizes can be significantly larger than with powder e.g. from 0.5 to 5 mm for pastilles and/or pellets and from 0.1 to 1 mm thick and from 2.5 to 10 mm in length and/or width, corresponding to a particle size (measured as the diameter of spheres of equal volume) of ca 1 to ca 6 mm. These larger particle forms form a further aspect of the invention. As for powders the level of fine particles in desirably low, in particular, the proportion of particles of size lower than 50 μm is less than 10% (by weight), desirably less than 2%, particularly less than 1%.

The following Examples illustrate the invention. All parts and percentages are by weight unless otherwise indicated. Examples of the invention are indicated by an Example number followed by a Run number and comparative Examples by a number including "C".

Materials

Emulsifiers

EM 1 Brij 72—HLB 4.9 stearyl alcohol 2-ethoxylate ex Uniqema
EM 2 Brij 721—HLB 15.5 stearyl alcohol 21-ethoxylate ex Uniqema
EM 3 Brij 78—HLB 15.3 stearyl alcohol 20-ethoxylate ex Uniqema
EM 4 3:2 by weight combination of Brij 72 and Brij 721
EM 5 Brij 700—HLB 18.8 stearyl alcohol 100-ethoxylate ex Uniqema
EM 6 Sisterna SP70-C—HLB 15 sucrose stearate/palmitate ester (ca 70% mono-ester) ex Sisterna
EM 7 Ryoto S-1570—HLB 15 sucrose stearate (ca 70% mono-ester) ex Ryoto
EM 8 Sisterna PS750—HLB 15 sucrose stearate/palmitate ester (ca 75% mono-ester) ex Sisterna
EM 9 Plurol WL 1009—polyglyceryl-6 distearate ex Gattefossé
EM 10 Atmos 150—mixture of glycerol mono stearate and glycerol distearate ex Uniqema
EM 11 Citrem FP 1201—citric acid/glycerol monostearate transesterification product ex Quest
EM 12 Sisterna SP80—HLB 15 sucrose stearate/palmitate ester (ca 80% mono-ester) ex Sisterna
EM 13 Arlatone 2121—1:1 mixture of sucrose cocoate and sorbitan stearate ex Uniqema
EM 14 Span 85—sorbitol tri-oleate ex Uniqema
EM 15 Arlasolve 200—iso-cetyl alcohol 20-ethoxylate ex Uniqema
EM 16 Arlatone T—sorbitan peroleate 40-ethoxylate ex Uniqema
EM 17 Arlacel P-135—polyhydroxystearate-PEG-polyhydroxystearate block copolymer polymeric surfactant ex Uniqema
EM 18 Synperonic PE/F127—PE/PO block copolymer surfactant ex Uniqema Polysaccharide Stabilisers (PS are Stabilisers of the invention; CS are comparative stabilisers)
PS 1 1:1 by wt Keltrol F—food grade Xanthan gum ex Kelco and *Konjak* PA—high purity (>90% pure) *Konjak* gum ex Dr W Behr
PS 2 Nutricol GP6621—commercial blend of Xanthan and *Konjak* gums (ca 60:40 by wt) including some dextrose ex FMC
PS 3 1:1 by wt Keltrol F and *Konjak* AS—a high viscosity potential *Konjak* gum ex Dr W Behr
PS 4 1:1 by wt Keltrol F and *Konjak* MS83 *Konjak* gum ex Dr W Behr
PS 5 1:1 by wt Keltrol F and *Konjak* MS119 *Konjak* gum ex Dr W Behr
PS 6 1:1 by wt Keltrol F and Nutricol GP 6220 *Konjak* gum ex FMC
PS 7 1:1 by wt Keltrol F and Nutricol GP 312 *Konjak* gum ex FMC
PS 8 1:1 by wt Keltrol T grade Xanthan gum ex Kelco and *Konjak* PA
PS 9 1:1 by wt Rhodopol SC grade Xanthan gum ex Rhone-Poulenc and *Konjak* PA
PS 10 1:1 by wt Rhodicare S grade Xanthan gum ex Rhone-Poulenc and *Konjak* PA
PS 11 1:1 by wt Keltrol TF Xanthan gum ex Kelco and Nutricol GP 312
PS 12 1:1 by wt Keltrol M and *Konjak* G-0467-98-1 ex FMC
PS 13 1:1 by wt Keltrol CG-F and *Konjak* G-0467-98-1
PS 14 1:1 by wt Keltrol M and Nutricol GP 312
PS 15 1:1 by wt Keltrol CG-F and Nutricol GP 312
PS 16 1:1 by wt Rhodopol SC and Leolex RX-H *Konjak* gum ex Shimizu
CS 1 1:1 by wt Keltrol F and Vidogum SP200—Tara gum ex Unipektin
CS 2 1:1 by wt Keltrol F+Vidogum L200—Locust bean gum ex Unipektin
CS 3 1:1 by wt Keltrol F+Vidogum GH175—Guar gum ex Unipektin
CS 4 Saladizer 250—commercial blend of Xanthan, Guar and Alginate gums ex Tic Gums
CS 5 Kelgum—commercial blend of Xanthan and Locust bean gums ex Kelco
CS 6 GFS—commercial blend of Xanthan, Locust bean and Guar gums ex Kelco Thickeners
TH 1 Structure Solanace—modified potato starch ex National Starch
TH 2 Laurex CS—cetearyl alcohol (mixed stearyl and cetyl alcohols)
TH 3 Stearic acid
TH 4 Structure Zea—hydroxypropyl distarch phosphate ex National Starch
TH 5 Vidogum SP200—Tara gum ex Unipektin
TH 6 *Konjak* PA
TH 7 Natrosol 250HHR—hydroxyethyl cellulose ex Hercules
TH 8 Jaguar HP-8—guar hydroxypropyl ether ex Rhone-Poulenc
TH 9 Avicel RC-591—sodium CMC and microcrystalline cellulose ex FMC
TH 10 Sea Spen—iota Carrageenan ex FMC
TH 11 Lunacera M—microcrystalline wax ex Fuller Oil/Emolient Materials
Oil 1 Arlamol M812—caprylic/capric triglyceride emollient oil ex Uniqema
Oil 2 Arlamol HD—isoparaffin emollient oil ex Uniqema
Oil 3 Arlamol E—stearyl alcohol 15-propoxylate emollient oil ex Uniqema
Oil 4 DC200 (350CS)—dimethicone silicone oil ex Dow Corning
Oil 5 DC200 (20CS)—dimethicone silicone oil ex Dow Corning
Oil 6 Eutanol G—octyl dodecanol ex Henkel
Oil 7 isopropyl palmitate
Oil 8 Jojoba oil
Oil 9 DC245—cyclomethicone silicone oil ex Dow Corning
Oil 10 mixture of: DC245 (15 parts); DC200 (4 parts) and DC1403 (a mixture of dimethicone and dimethiconol silicone oils ex Dow Corning) (1 part)
Oil 11 liquid paraffin oil
Oil 12 Estol 3609—triethylhexanoin ex Uniqema
Oil 13 Pripure 3759—squalane ex Uniqema
Oil 14 Prisorine 2021—isopropyl isostearate ex Uniqema Other Components
Preservatives
Pre 1 Germaben II—preservative ex Sutton
Pre 2 Nipaguard BPX—preservative ex Nipa
Pre 3 Phenoxyethanol ex Nipa
Pre 4 Nipaguard DMDMH—DMDM Hydantoin ex Nipa Other Additives
Add 1 Glycerol—humectant
Add 2 Dragosantol—bisabolol ex Dragoco
Add 3 D-Panthenol ex BASF
Add 4 Perfume Floral/Oriental (AF27536) ex Quest NV
Add 5 Perfume Citrus/Herbal (AF27450) ex Quest NV
Add 6 Urea
Add 7 DHA—dihydroxy acetone (50 wt % aqueous solution)
Add 8 Ethyl alcohol
Add 9 Atlas G-2330 ex Uniqema
Add 10 Propylene glycol
Add 11 PEG 400
Add 12 PEG 1500
Add 13 Parsol MCX—octylmethoxycinnamate ex Givaudin
Add 14 Parsol 1789—butylmethoxydibenzoyl methane ex Givaudin
Add 15 Parsol 5000—4-methylbenzylidene camphor ex Givaudin
Add 16 Tioveil AQ—polyacrylate stabilised aqueous suspension of titanium dioxide ex Uniqema
Add 17 mixture of water dispersible pigments; titanium dioxide (10 parts); yellow iron oxide (2 parts); red iron oxide (0.4 parts); and black iron oxide (0.25 parts)
Add 18 Hombitec H—titanium dioxide pigment ex Sachtleben
Add 19 Tioveil FIN—ultrafine titanium dioxide and alumina suspension in alkyl benzoates and polyhydroxystearic acid ex Uniqema
Add 20 Spectraveil FIN—fine zinc oxide suspension in alkyl benzoates and polyhydroxystearic acid ex Uniqema
Add 21 DEET—diethyl toluamide insect repellant
Add 22 Citronella Oil
water demineralised water Formulation Methods
Hot dispersion—Milks
The Xanthan and *Konjak* gum powders were dispersed into water at 80° C., the emulsifier system was added to the water and mixed for 20 minutes. The oil components were mixed and added as an oil phase to the mixture at 80° C. (with heating if necessary), the mixture was homogenised for 2 minutes in an Ultra-Turrax mixer at 8000 rpm (ca 133 Hz) at 80° C. and the emulsion then allowed to cool to ambient temperature under gentle stirring.
Cold Dispersion—Milks
The Xanthan and *Konjak* gum powders were pre-blended to form a powder (with milling of the *Konjak* if necessary) and the blended powder was dispersed into water at ambient temperature, the emulsifier system was added to the water and mixed for 20 minutes. The oil components were mixed and added as an oil phase to the mixture at ambient temperature, the mixture was homogenised for 2 minutes in an Ultra-Turrax mixer at 8000 rpm (ca 133 Hz) at ambient temperature (without specific heating) and then gently stirred for a few minutes.
Hot Dispersion—Creams
The Xanthan and *Konjak* gum powders were dispersed into water at 80° C. and the high HLB emulsifier added and mixed for 20 minutes at 80° C. The low HLB emulsifier was added to a mixture of the oil components forming the oil phase and heated to 80° C. The thickener followed by the oil phase were then added to the water phase under stirring. The mixture was then homogenised for 2 minutes in an Ultra-Turrax mixer at 8000 rpm (ca 133 Hz) at 80° C. and the emulsion then allowed to cool to ambient temperature under gentle stirring.

Cold Dispersion—Creams
The Xanthan and *Konjak* gum powders were dispersed into water at ambient temperature and the high HLB emulsifier added and mixed for 20 minutes at ambient temperature. The low HLB emulsifier was added to a mixture of the oil components forming the oil phase. The thickener component(s) were added to the aqueous phase and the oil phase was then added under stirring. The mixture was then homogenised for 2 minutes in an Ultra-Turrax mixer at 8000 rpm (ca 133 Hz) at ambient temperature (without specific heating) and then gently stirred for a few minutes.

Test Methods:

Viscosity was measured with a Brookfield RVDVI+ viscometer using an appropriate spindle (RV2, RV3, RV4 or RV 6—depending on the viscosity of the emulsion being tested) at 6 rpm (0.1 Hz), 1 day after making the emulsions and results are quoted in mPa.s.

Stability was assessed by observing the emulsions after storage at ambient temperature (Amb), cold at 5° C. or under elevated temperature storage at 40° C. and 50° C. Measuring storage stability at 50° C. is a very severe test. The times at which assessments of stability or measurements of viscosity were made are abbreviated with "D"=day; "W"=week; and "M"=month; a "0" for stability indicates that the emulsion could not be satisfactorily made or that it broke before the first assessment was made.

Appearance (abbreviated "appear") was assessed visually and by skin feel using the following ratings:
1 very good has appearance highly suitable for end use and good skin feel with good shear thinning
2 good has appearance suitable for end use and moderate skin feel with some shear thinning
3 acceptable appearance and skin feel are acceptable for end use
4 poor appearance somewhat slimy and/or stringy and skin feel not particularly good
5 very poor appearance very slimy and stringy and poor skin feel State the fluidity of the product emulsions was assesses visually and the comments are descriptive in relation to the intended product type (milk, cream etc.).

Droplet size was visually assessed with a Zeiss Jenalumar microscope under polarised Tight using coloured lambda filters. Results are quoted as a range for the majority of particles in microns ($\mu$m).

EXAMPLE 1

Liquid cosmetic milk oil in water emulsion formulations were made up, using the hot process described above for making milk emulsions. The emulsion compositions are set out in Table 1a and the results of testing in Table 1b below.

TABLE 1a

| | Formulation Components - (% by weight) | | | | | |
|---|---|---|---|---|---|---|
| Ex No | EM 1 | EM 2 | PS 1 | Oil 1 | Pre 1 | water |
| 1.C.1 | 0.7 | 0.3 | — | 20 | 1 | to 100 |
| 1.1 | 0.69 | 0.29 | 0.02 | 20 | 1 | to 100 |
| 1.2 | 0.67 | 0.29 | 0.06 | 20 | 1 | to 100 |
| 1.3 | 0.63 | 0.27 | 0.1 | 20 | 1 | to 100 |
| 1.4 | 0.48 | 0.48 | 0.06 | 20 | 1 | to 100 |
| 1.5 | 0.95 | — | 0.06 | 20 | 1 | to 100 |
| 1.6 | — | 0.95 | 0.06 | 20 | 1 | to 100 |

TABLE 1b

| | Visc | | Stability | | | drop size | Comments | |
|---|---|---|---|---|---|---|---|---|
| Ex No | (mPa · s) | pH | Amb | 5° C. | 40° C. | 50° C. | (μm) | state | appear. |
| 1.C.1 | — | — | 0 | 0 | 0 | 0 | 10–50 | v liquid | — |
| 1.1 | 783.3 | 6.8 | >6 M | >3 M | >1 M | 1 W | 10–50 | v liquid | 1 |
| 1.2 | 1583 | 6.9 | >6 M | >3 M | >3 M | 2 W | 10–50 | liquid | 2 |
| 1.3 | 3166 | 6.9 | >6 M | >3 M | >3 M | >3 M | 10–50 | liquid | 3 |
| 1.4 | 3133 | 6.8 | >6 M | >3 M | >3 M | 2 W | 5–30 | liquid | 2 |
| 1.5 | 1200 | 6.3 | >6 M | >3 M | >3 M | >3 M | 10–50 | liquid | 3 |
| 1.6 | 2233 | 6.3 | 4 M | >3 M | >3 M | 2 W | 5–30 | liquid | 2 |

These formulations show that in the absence of the polysaccharide stabiliser, at 1% emulsifier, the emulsion was not stable against creaming and rapid (in less than one day) breaking. The inclusion of even very low levels of polysaccharide stabiliser gave emulsions with extended stability even at elevated temperatures.

EXAMPLE 2

A series of emulsions was made up using various polysaccharide stabilisers, in combination with an alcohol ethoxylate emulsifier, using the hot process described above for making milk emulsions. The compositions are set out in Table 2a and the results of testing in Table 2b below.

TABLE 2a

| | EM 3 | Stabiliser | | Oil 1 | Pre 1 | water |
|---|---|---|---|---|---|---|
| Ex No | (wt %) | type | (wt %) | (wt %) | (wt %) | (wt %) |
| 2.1 | 0.05 | PS 1 | 0.06 | 20 | 1 | to 100 |
| 2.C.1 | 0.05 | CS 1 | 0.06 | 20 | 1 | to 100 |
| 2.C.2 | 0.05 | CS 2 | 0.06 | 20 | 1 | to 100 |
| 2.C.3 | 0.05 | CS 3 | 0.06 | 20 | 1 | to 100 |
| 2.2 | 0.05 | PS 2 | 0.05 | 20 | 1 | to 100 |
| 2.C.4 | 0.05 | CS 4 | 0.05 | 20 | 1 | to 100 |
| 2.C.5 | 0.05 | CS 5 | 0.05 | 20 | 1 | to 100 |
| 2.C.6 | 0.05 | CS 6 | 0.05 | 20 | 1 | to 100 |

TABLE 2b

| | | Viscosity | Stability | | Comments | |
|---|---|---|---|---|---|---|
| Ex No | pH | (mPa · s) | Amb | 50° C. | state | appear |
| 2.1 | 6.9 | 1833 | >6 M | >3 M | fluid | 2 |
| 2.C.1 | 7.1 | 2500 | 2 M | 0 | fluid | 2 |
| 2.C.2 | 7.2 | 2400 | 2 W | 3 D | fluid | 4 |
| 2.C.3 | 7.2 | — | 0 | — | very fluid | 2 |
| 2.2 | 6.9 | 3066 | >6 M | 6 W | fluid | 2 |
| 2.C.4 | 7.3 | — | 0 | — | very fluid | 2 |
| 2.C.5 | 7.2 | 3133 | 2 W | 0 | fluid | 5 |
| 2.C.6 | 7.1 | 4800 | 2 W | 0 | fluid | 5 |

These results show that the use of a combination of polyglucomannan and Xanthan as the polysaccharide stabiliser gives stable emulsions, whereas the other combinations give emulsions having poor stability (at best).

EXAMPLE 3

In this Example, emulsions were made up using the hot method incorporating various amounts of *Konjak* gum (*Konjak* PA) and Xanthan (Keltrol F) as the polysaccharide stabiliser were included in a basic aqueous emulsion including 0.05% emulsifier EM 3, 20% emollient Oil 1, 1% preservative Pre 1 with water to 100%. The amounts of *Konjak* PA, Keltrol F and the weight ratio of the two is included in Table 3 below. From the table it can be seen that the best stability of the emulsions is obtained when the weight ratio between *Konjak* gum and Xanthan gum in the polysaccharide stabiliser is about 50:50. For the emulsions containing 0.05% total stabiliser, those containing no polysaccharide stabiliser or one only of *Konjak* and Xanthan did not give emulsions that were stable enough to test. Where both polymers were used, stability improves as the ratio approaches 50:50; those in the range 30:70 to 70:30 having generally good stability. Similarly, the appearance improves as the ratio approaches 50:50; those in the range 30:70 to 70:30 having generally good appearance. For the emulsions containing 0.5% total stabiliser, the emulsion made using *Konjak* alone had poor stability although its appearance was good; the emulsion made using Xanthan alone had moderately good stability, but poor appearance; and the emulsion made using equal amounts of *Konjak* and Xanthan gave very good stability, but had poor appearance. This suggests that the use of more Konjac/Xanthan than needed to provide emulsion stability contributes to thickening with a rheological profile that is not particularly attractive for personal care applications.

TABLE 3

| Ex No | Konjac (wt %) | Xanthan (wt %) | ratio | pH | Viscosity (mPa·s) | Stability Amb | 5° C. | 40° C. | 50° C. |
|---|---|---|---|---|---|---|---|---|---|
| 3.C.1 | — | — | — | — | * | 0 | 0 | 0 | 0 |
| 3.C.2 | 0.05 | 0 | 100:0 | — | * | 0 | 0 | 0 | 0 |
| 3.1 | 0.045 | 0.005 | 90:10 | 6.7 | 2816 | >3 M | >3 M | >3 M | >3 M |
| 3.2 | 0.035 | 0.015 | 70:30 | 6.7 | 4816 | >3 M | >3 M | >3 M | >3 M |
| 3.3 | 0.025 | 0.025 | 50:50 | 6.7 | 1735 | >3 M | >3 M | >3 M | >3 M |
| 3.4 | 0.015 | 0.035 | 30:70 | 6.7 | 2416 | >3 M | >3 M | >3 M | >3 M |
| 3.5 | 0.005 | 0.045 | 10:90 | 6.7 | 3450 | >3 M | >3 M | >3 M | >3 M |
| 3.C.3 | 0 | 0.05 | 0:100 | — | * | 0 | 0 | 0 | 0 |
| 3.C.4 | 0.5 | 0 | 100:0 | 6.6 | 4500 | 1 M | 1 M | 0 | 0 |
| 3.6 | 0.25 | 0.25 | 50:50 | 6.7 | ** | >3 M | >3 M | >3 M | >3 M |
| 3.C.5 | 0 | 0.5 | 0:100 | 6.7 | 2033 | >3 M | >3 M | 2 M | 2 W |

*stable emulsion not made
**emulsion viscosity too high for measurement on Brookfield RDVI+

EXAMPLE 4

In this Example a number of emulsions are made up using various amounts of emulsifier using the hot emulsification method described above for milk type emulsions The compositions are set out in Table 4a and the results of testing in Table 4b below. These data indicate that the use of emulsifier much in excess of that needed to emulsify the oil phase the may have a deleterious effect on emulsion stability.

TABLE 4a

| Ex No | EM 3 (wt %) | PS 1 (wt %) | Oil 1 (wt %) | Pre 1 (wt %) | water |
|---|---|---|---|---|---|
| 4.C.1 | — | 0.06 | 20 | 1 | to 100 |
| 4.1 | 0.05 | 0.06 | 20 | 1 | to 100 |
| 4.2 | 0.5 | 0.06 | 20 | 1 | to 100 |
| 4.3 | 1 | 0.06 | 20 | 1 | to 100 |

TABLE 4b

| Ex No | pH | Visc (mPa·s) | Stability Amb | 50° C. | drop size (μm) | Comments |
|---|---|---|---|---|---|---|
| 4.C.1 | 7 | * | 0 | 0 | >100 | No emulsion |
| 4.1 | 6.9 | 1766 | >3 M | >3 M | 10–50 | Fluid |
| 4.2 | 6.6 | 1366 | >3 M | 2 M | 10–30 | Fluid |
| 4.3 | 6.7 | 1333 | >3 M | 1 M | 10–15 | Fluid |

*stable emulsion not made

EXAMPLE 5

Liquid cosmetic milk oil in water emulsion formulations were made up using the formulations set out in Table 5a below using the hot process described above for making milk emulsions using fatty acid esters of naturally occurring polyhydroxylic materials. A comparison using no emulsifier, 5.C.1, was run, but a stable emulsion could not be made without the emulsifier. The results, set out in Table 5b below, show that stable emulsions can readily be made notably with sucrose esters, particularly high mono-ester content sucrose esters. The level of emulsifier needed is higher than the minimum needed with alcohol ethoxylate emulsifiers in cosmetic milk formulations with the triglyceride oil Arlamol M812 (Oil 1). As with alcohol ethoxylates there is a plateau of emulsion stability, for these emulsifiers at about 0.5 to about 1% by weight of the emulsion. The polyglycerol ester can form an emulsion of moderate stability and thus appears to be a less effective emulsifier than the sucrose esters in this type of system.

TABLE 5a

| Ex No | Emulsifier type | (wt %) | PS 1 (wt %) | Oil 1 (wt %) | Pre 1 (wt %) | water |
|---|---|---|---|---|---|---|
| 5.C.1 | — | — | 0.06 | 20 | 1 | to 100 |
| 5.1 | EM 6 | 0.5 | 0.06 | 20 | 1 | to 100 |
| 5.2 | EM 6 | 1 | 0.06 | 20 | 1 | to 100 |
| 5.3 | EM 6 | 5 | 0.06 | 20 | 1 | to 100 |
| 5.4 | EM 6 | 0.95 | 0.05 | 20 | 1 | to 100 |
| 5.5 | EM 7 | 0.95 | 0.05 | 20 | 1 | to 100 |
| 5.6 | EM 9 | 0.95 | 0.05 | 20 | 1 | to 100 |
| 5.7 | EM 8 | 0.95 | 0.05 | 20 | 1 | to 100 |

TABLE 5b

| Ex No | pH | Visc (mPa·s) | Stability Amb | 5° C. | 40° C. | 50° C. | drop size (μm) | Comments state | appear |
|---|---|---|---|---|---|---|---|---|---|
| 5.C.1 | 7.0 | — | 0 | 0 | 0 | 0 | >100 | — | — |
| 5.1 | 6.7 | 1033 | >3 M | >3 M | >3 M | >3 M | 10–100 | Fluid milk | 1 |
| 5.2 | 6.5 | 867 | >3 M | >3 M | >3 M | >3 M | 10–30 | Fluid milk | 1 |
| 5.3 | 6.3 | 5300 | >3 M | >3 M | 2 M | 1 M | 10–30 | Milk | 2 |
| 5.4 | 7.2 | 600 | >6 M | >6 M | 2 M | 1 M | 20–50 | v fluid milk | 2 |
| 5.5 | 6.5 | 887 | >6 M | >6 M | >6 M | 2 M | 5–15 | v fluid milk | 1 |

TABLE 5b-continued

| Ex No | pH | Visc (mPa·s) | Stability Amb | 5° C. | 40° C. | 50° C. | drop size (μm) | Comments state | appear |
|---|---|---|---|---|---|---|---|---|---|
| 5.6 | 7.6 | 1466 | >6 M | >6 M | >6 M | 2 M | 20–50 | fluid milk | 3 |
| 5.7 | 7.1 | 900 | >6 M | >6 M | 2 M | 1 M | 1–15 | v fluid milk | 1 |

EXAMPLE 6

This Example compares the hot and cold emulsification methods of making emulsions of the invention. Examples 6.1 to 6.3 were made by the hot emulsification method, Examples 6.4 to 6.6 were made by the cold emulsification method using the same level of polysaccharide stabiliser and Examples 6.7 to 6.9 were made by the cold emulsification route using a higher level of polysaccharide stabiliser. The results indicate that emulsions can be made by either route, but that cold emulsification gives somewhat coarser emulsions which may have lower stability unless the increased level of polysaccharide stabiliser is used.

TABLE 6a

| Ex No | Disp Temp | Emulsifier type | Emulsifier (wt %) | PS 1 (wt %) | Oil 1 (wt %) | Pre 1 (wt %) | Water (wt %) |
|---|---|---|---|---|---|---|---|
| 6.1 | Hot | EM 6 | 0.95 | 0.05 | 20 | 1 | to 100 |
| 6.2 | Hot | EM 7 | 0.95 | 0.05 | 20 | 1 | to 100 |
| 6.3 | Hot | EM 8 | 0.95 | 0.05 | 20 | 1 | to 100 |
| 6.4 | Cold | EM 6 | 0.95 | 0.05 | 20 | 1 | to 100 |
| 6.5 | Cold | EM 7 | 0.95 | 0.05 | 20 | 1 | to 100 |
| 6.6 | Cold | EM 8 | 0.95 | 0.05 | 20 | 1 | to 100 |
| 6.7 | Cold | EM 6 | 0.95 | 0.1 | 20 | 1 | to 100 |
| 6.8 | Cold | EM 7 | 0.95 | 0.1 | 20 | 1 | to 100 |
| 6.9 | Cold | EM 8 | 0.95 | 0.1 | 20 | 1 | to 100 |

TABLE 6b

| Ex No | pH | Visc (mPa·s) | Stability Amb | 50° C. | drop size (μm) | State | Colour | Powder | Disp | residue |
|---|---|---|---|---|---|---|---|---|---|---|
| 6.1 | 7 2 | 600 | >6 M | 1 M | 20–50 | v liquid | Yellow | fine | easy | none |
| 6 2 | 6.5 | 867 | >6 M | 2 M | 5–15 | v liquid | White | fine | easy | none |
| 6 3 | 7.1 | 900 | >6 M | 1 M | 1–5 | v liquid | White | fine | v easy | none |
| 6 4 | 7 5 | 400 | 5 M | 3 W | 10–50 | v liquid | sl yellow | fine | easy | some |
| 6.5 | 7.1 | 800 | >6 M | 3 W | 10–30 | fluid | white | fine | easy | little |
| 6.6 | 7.5 | 600 | 5 M | 1 W | 10–30 | v thin | white | fine | v easy | none |
| 6.7 | 7.4 | 2066 | >6 M | 5 W | 10–30 | liquid | sl yellow | fine | easy | some |
| 6.8 | 7.1 | 4166 | >6 M | 2 M | 10–30 | liquid | white | fine | easy | little |
| 6.9 | 7 4 | 1733 | >6 M | 6 W | 5–20 | liquid | white | fine | v easy | none |

Colour indicates the colour of the blended Xanthan Konjak powders
Powder indicates the state of subdivision of the blended Xanthan Konjak powders
Disp indicates how easily the blended Xanthan Konjak powders dispersed in the water under high intensity mixing
Residue indicates how much Xanthan or Konjak was left as a residue after high intensity mixing.

EXAMPLE 7

This Example illustrates emulsion creams i.e. emulsions of relatively high viscosity, which are thickened by the inclusion of amphiphilic materials and/or waxes, were made by the hot dispersion route and stabilised according to the invention. For this Example the oil phase including amphiphilic thickening materials had the following composition:

| Material Oil components | wt parts | Material Thickener components | wt parts |
|---|---|---|---|
| Oil 7 | 4 | TH 2 | 4 |
| Oil 8 | 1 | TH 3 | 3 |
| Oil 2 | 1 | TH 10 | 3 |
| Oil 6 | 2 | | |
| Oil 5 | 1 | | |

Formulation 7.C.1 is emulsified/stabilised by alcohol ethoxylate surfactants at a conventional level (5% of the total emulsion) for this type of product. Example 7.1 uses a similar level of emulsifier with Xanthan/Konjak as stabiliser. Examples 7.2 to 7.5 use Xanthan/Konjak as stabiliser and alcohol ethoxylate emulsifiers having a range of HLB values at more nearly optimised levels (1% total emulsifier and stabiliser) for this type of product according to the invention. Using emulsifier EM 5, the viscosity of the cream initially produced was relatively low (the product had the consistence of a thick milk) so the Example was re-run as 7.4 including a supplementary thickener (TH 1). The resulting product has a viscosity similar to that of the reference with a lighter skin feel. In Examples 7.6 and 7.7 and the associated comparative runs, a small amount of alkali (10% aqueous NaOH) was added to raise the pH to about 6.5. This provided a modest improvement in stability when using Brij 78.

In terms of stability, the stability of 7.1 is somewhat better than that of the reference, but the improved stability obtained using lower levels of emulsifier indicate that large amounts of emulsifier, beyond that necessary to provide adequate emulsification, can interfere with the stabilising effect of the polysaccharide stabiliser combination. Example 7.1 to 7 4 also indicate that, for this type of oil phase, relatively more hydrophilic emulsifiers give better results.

Examples 7.5 to 7.7 confirm that emulsifiers of slightly lower HLB can be used although the stability results are not quite as good. In Examples 7.8 and 7.9, sucrose esters (high mono-esters) were used as the emulsifiers, the cream products had good stability, appearance and skin feel and satisfactory viscosity although somewhat lower than obtained using the alcohol ethoxylate emulsifiers. The Formulations of the Example are set out in Table 7a and the testing results in Table 7b below.

TABLE 7a

| Ex No | Oil phase | Emulsifier type | (wt %) | TH 1 (wt %) | PS 1 (wt %) | Add 1 | Pre 2 | Add 2 | Add 3 | Water |
|---|---|---|---|---|---|---|---|---|---|---|
| 7.C.1 | 19 | EM 4 | 5 | — | — | 4 | 0.7 | 1 | 0.5 | to 100 |
| 7.1 | 19 | EM 4 | 5 | — | 0.06 | 4 | 0.7 | 1 | 0 5 | to 100 |
| 7.2 | 19 | EM 5 | 0.95 | — | 0.05 | 4 | 0.7 | 1 | 0.5 | to 100 |
| 7.3 | 19 | EM 3 | 0.95 | — | 0.05 | 4 | 0.7 | 1 | 0.5 | to 100 |
| 7.4 | 19 | EM 5 | 0.95 | 2 | 0.05 | 4 | 0.7 | 1 | 0.5 | to 100 |
| 7.5 | 19 | EM 3 | 0.95 | — | 0.05 | 4 | 0.7 | 1 | 0.5 | to 100 |
| 7.6 | 19 | EM 3 | 0.95 | — | 0.05 | 4 | 0.7 | 1 | 0.5 | [2]to 100 |
| 7.C.2 | 19 | EM 3 | 1 | — | — | 4 | 0.7 | 1 | 0.5 | [2]to 100 |
| 7.7 | 24[1] | EM 3 | 0.95 | — | 0.05 | 4 | 0.7 | 1 | 0.5 | [2]to 100 |
| 7.C.3 | 24[1] | EM 3 | 1 | — | — | 4 | 0.7 | 1 | 0.5 | [2]to 100 |
| 7.8 | 19 | EM 6 | 0.95 | — | 0.05 | 4 | 0.7 | 1 | 0.5 | to 100 |
| 7.9 | 19 | EM 6 | 0.95 | — | 0.05 | 4 | 0.7 | 1 | 0.5 | to 100 |

[1]Additional amphiphile thickeners were included - 2% TH 2 and 3% TH 3
[2]ca 0.05% 10% aqueous NaOH solution was added to increase the pH TABLE 7b

| Ex No | HLB | Viscosity (mPa · s) | pH | Amb | 5° C. | 40° C. | 50° C. | Comments state | appear |
|---|---|---|---|---|---|---|---|---|---|
| 7.C.1 | ca 9 | 74500 | 4.5 | >6 M | >3 M | 3 M | 2 D | visc cream | 3 |
| 7.1 | ca 9 | 75600 | 4.5 | >6 M | >3 M | >3 M | 1 W | visc cream | 3 |
| 7.2 | 18.8 | 19660 | 4.5 | >6 M | >3 M | >3 M | 2 W | thin cream | 2 |
| 7.3 | 15.3 | 42660 | 4.3 | >6 M | >3 M | >3 M | 1 W | cream | 1 |
| 7.4 | 18.8 | 76500 | 5.0 | >6 M | >3 M | >3 M | >2 M | visc cream | 1 |
| 7.5 | 15.3 | 42660 | 4.0 | >3 M | >3 M | 3 M | 1 W | cream | 1 |
| 7 6 | 15.3 | 37500 | 6.5 | >3 M | >3 M | >3 M | 2 W | cream | 1 |
| 7.C.2 | 15.3 | 35600 | 6.5 | >3 M | >3 M | 1 M | 0 | cream | 1 |
| 7.7 | 15.3 | 43830 | 6.5 | >3 M | >3 M | >3 M | 1 W | cream | 1 |
| 7 C.3 | 15.3 | 42560 | 6 5 | >3 M | >3 M | >3 M | 0 | cream | 1 |
| 7 8 | 15 | 41133 | 4.6 | >3 M | >3 M | >3 M | 2 M | cream | 1 |
| 7 9 | 16 | 52820 | 4 7 | >3 M | >3 M | >3 M | 2 M | visc cream | 1 |

EXAMPLE 8

This Example illustrates creams i.e. emulsions of relatively high viscosity, made by the cold dispersion route, which are thickened by the inclusion of polymeric thickeners, stabilised according to the invention.

TABLE 8a

| Ex No | EM 8 (wt %) | PS 1 (wt %) | Thickener type | (wt %) | Oil 1 (wt %) | Pre 1 (wt %) | water (wt %) |
|---|---|---|---|---|---|---|---|
| 8.1 | 0.45 | 0.05 | TH 5 | 0.5 | 20 | 1 | to 100 |
| 8.2 | 0.45 | 0.05 | TH 6 | 0.5 | 20 | 1 | to 100 |
| 8.3 | 0.45 | 0.05 | TH 7 | 0.5 | 20 | 1 | to 100 |
| 8.4 | 0.45 | 0.05 | TH 8 | 0.5 | 20 | 1 | to 100 |
| 8.5 | 0.45 | 0.05 | TH 9 | 0.5 | 20 | 1 | to 100 |
| 8.6 | 0.45 | 0.05 | TH 10 | 0.5 | 20 | 1 | to 100 |

TABLE 8b

| Ex No | pH | Viscosity (mPa · s) | Amb | 5° C. | 40° C. | 50° C. | Droplet size μm | appear |
|---|---|---|---|---|---|---|---|---|
| 8.1 | 7.1 | 6800 | >3 M | >3 M | >3 M | 2 M | 1–5 | 3 |
| 8.2 | 6.7 | 18660 | >3 M | >3 M | 2 M | 1 M | 1–10 | 4 |
| 8.3 | 6.9 | 6033 | >3 M | >3 M | >3 M | 2 M | 5–15 | 3 |
| 8.4 | 7.5 | 5633 | >3 M | >3 M | >3 M | 1 M | 5–20 | 3 |
| 8.5 | 7.2 | 2100 | >3 M | >3 M | >3 M | 2 W | 50–100 | 3 |
| 8.6 | 6.9 | 11730 | >3 M | >3 M | >3 M | >1 W | 5–15 | 4 |

EXAMPLE 9

This Example investigates the effect of pH and electrolyte on the stability of emulsions made by the hot dispersion route. The basic formulation used was that of Example 3.1 (Examples 9.4 and 9.8). In Examples 9.1 to 9.3 pH was reduced by adding lactic acid and in Examples 9.5 to 9.7 it was increased by adding sodium hydroxide. In Examples 9.8 to 9.10 increasing amounts of salt (NaCl) were added to the composition to test stability. Table 9 below sets out the properties and stability testing results for the emulsions obtained. These data show that the emulsions become progressively less stable as the pH is reduced; the effect is particularly marked when the pH is reduced below 4, At alkali pH's the emulsions become less stable, but remain stable even when the pH is above 9 except under the extreme conditions of storage at 50° C., when the emulsion is moderately stable, but becomes discoloured (yellow) indicating that chemical degradation of some of the components has occurred. The emulsions also become less stable as the salt concentration is increased. Indicating that the Xanthan/*Konjak* stabilisation is sensitive to electrolyte

TABLE 9

| Ex No | pH | NaCl (wt %) | molar | Viscosity (mPa · s) | Stability Amb | 5° C. | 40° C. | 50° C. |
|---|---|---|---|---|---|---|---|---|
| 9.1 | 3.0 | — | — | — | 0 | 0 | 0 | 0 |
| 9.2 | 3.4 | — | — | 1700 | 2 M | >3 M | 0 | 0 |
| 9.3 | 4.0 | — | — | 3566 | >3 M | >3 M | >3 M | 1 D |
| 9.4 | 6.9 | — | — | 3866 | >3 M | >3 M | >3 M | >3 M |
| 9.5 | 7.3 | — | — | 3166 | >3 M | >3 M | >3 M | >3 M |
| 9.6 | 7.7 | — | — | 2666 | >3 M | >3 M | >3 M | >3 M |
| 9.7 | 9.3 | — | — | 1466 | >3 M | >3 M | >3 M | 2 M |
| 9.8 | 6.9 | 0 | 0 | 3866 | >3 M | >3 M | >3 M | >3 M |
| 9 9 | 6.7 | 0.1 | 0.017 | — | 1 W | 0 | 0 | 0 |
| 9.10 | 6.5 | 0.3 | 0.051 | — | 3 D | 0 | 0 | 0 |

EXAMPLE 10

In this Example the effect of including perfume and preservative additives of types commonly used in personal care emulsions made by the hot dispersion route is investigated. The compositions used are set out in Table 10a and the testing results in Table 10b below.

TABLE 10a

| Ex No | EM 3 (wt %) | PS 1 (wt %) | Additive Type | (wt %) | Oil 1 (wt %) | Pre 1 (wt %) | Water (wt %) |
|---|---|---|---|---|---|---|---|
| 10.1 | 0.05 | 0.05 | Add 4 | 0.2 | 20 | 1 | to 100 |
| 10.2 | 0.05 | 0.05 | Add 4 | 0.5 | 20 | 1 | to 100 |
| 10.3 | 0.05 | 0.05 | Add 5 | 0.2 | 20 | 1 | to 100 |
| 10.4 | 0.05 | 0.05 | Add 5 | 0.5 | 20 | 1 | to 100 |
| 10.5 | 0.05 | 0.05 | Pre 1 | 1 | 20 | — | to 100 |
| 10.6 | 0.05 | 0.05 | Pre 2 | 1 | 20 | — | to 100 |
| 10.7 | 0.05 | 0.05 | Pre 3 | 1 | 20 | — | to 100 |
| 10.8 | 0.05 | 0.05 | Pre 4 | 1 | 20 | — | to 100 |

TABLE 10b

| Ex No | pH | Viscosity (mPa · s) | Stability Amb | 5° C. | 40° C. | 50° C. | Comments |
|---|---|---|---|---|---|---|---|
| 10.1 | 6.6 | 1000 | >3 M | >3 M | >3 M | 2 M | Fluid milk |
| 10 2 | 6 4 | 1066 | >3 M | >3 M | >3 M | 3 W | Fluid milk |
| 10.3 | 6.4 | 933 | >3 M | >3 M | >3 M | 1 M | Fluid milk |
| 10.4 | 6 4 | 1000 | >3 M | >3 M | >3 M | 2 W | Fluid milk |
| 10.5 | 6.8 | 1833 | >3 M | >3 M | >3 M | >3 M | Fluid milk |
| 10 6 | 6 4 | 3900 | >3 M | >3 M | >3 M | 2 W | Fluid milk |
| 10 7 | 6 4 | 3866 | >3 M | >3 M | >3 M | >3 M | Fluid milk |
| 10 8 | 6 2 | 3066 | >3 M | >3 M | >3 M | >3 M | Fluid milk |

EXAMPLE 11

This Example compares the emulsification and stability of compositions including a range of emollient oils, of differing polarity, and includes a comparison of a Xanthan/*Konjak* combination against a Xanthan/Locust Bean Gum combination as emulsion stabilisers. The emulsions were made by the hot dispersion route. The compositions of the test emulsions are set out in Table 11a and the results from testing in Table 11b below. Examples 11.4 to 11.7 includes compositions made using minimum amounts of emulsifier and for the particularly non-polar Oil 2 (Arlamol E) in Example 11.5, the amount of emulsifier/stabiliser is lower than would be desirable in a practical system for optimum stability. It was also noted that in Example 11.7 using Oil 4 (dimethicone oil) the emulsification was not very good with relatively large oil drops. The droplet size could be reduced by using a higher level of emulsifier.

TABLE 11 a

| Ex No | EM 3 (wt %) | Stabiliser type | (wt %) | Oil type | (wt %) | Pre 1 (wt %) | Water (wt %) |
|---|---|---|---|---|---|---|---|
| 11.1 | 0.05 | PS 1 | 0.1 | Oil 1 | 20 | 1 | to 100 |
| 11.2 | 0.05 | PS 1 | 0.1 | Oil 2 | 20 | 1 | to 100 |
| 11.3 | 0.05 | PS 1 | 0.1 | Oil 3 | 20 | 1 | to 100 |
| 11.C.1 | 0.05 | CS 2 | 0.1 | Oil 1 | 20 | 1 | to 100 |
| 11.C.2 | 0.05 | CS 2 | 0.1 | Oil 2 | 20 | 1 | to 100 |
| 11.C.3 | 0.05 | CS 2 | 0.1 | Oil 3 | 20 | 1 | to 100 |
| 11.4 | 0.05 | PS 1 | 0.05 | Oil 1 | 20 | 1 | to 100 |
| 11.5 | 0.05 | PS 1 | 0.05 | Oil 2 | 20 | 1 | to 100 |
| 11.6 | 0.05 | PS 1 | 0.05 | Oil 3 | 20 | 1 | to 100 |
| 11.7 | 0.05 | PS 1 | 0.05 | Oil 4 | 20 | 1 | to 100 |

TABLE 11b

| Ex No | pH | Viscosity (mPa·s) | Stability Amb | 5° C. | 40° C. | 50° C. | Comments Colour | state | appear |
|---|---|---|---|---|---|---|---|---|---|
| 11.1 | 6.8 | 3333 | >6 M | >3 M | >3 M | >3 M | White | Fluid milk | 2 |
| 11.2 | 6.9 | 3600 | >6 M | >3 M | >3 M | 2 M | White | Fluid milk | 2 |
| 11.3 | 5.6 | 3400 | >6 M | >3 M | >3 M | >3 M | White | Fluid milk | 2 |
| 11.C.1 | 7.2 | 6800 | >6 M | >3 M | 1 M | 1 W | White | Milk | 5 |
| 11.C.2 | 7.0 | 6400 | 5 M | >3 M | 2 W | 1 W | White | Milk | 5 |
| 11.C.3 | 5.5 | 6333 | 2 M | >3 M | 2 W | 2 D | White | Milk | 5 |
| 11.4 | 6.8 | 1833 | >3 M | >3 M | >3 M | >3 M | White | Fluid milk | 2 |
| 11.5 | 6.7 | 1500 | 2 M | >3 M | 1 M | 1 M | White | Fluid milk | 2 |
| 11.6 | 5.6 | 2033 | >3 M | >3 M | >3 M | >3 M | White | Fluid milk | 2 |
| 11.7 | 6.5 | 1000 | >3 M | >3 M | >3 M | >3 M | Grey | translucent | 3 |

EXAMPLE 12

In this Example the effect of including water soluble additives, co-solvents and chemical and physical sunfilters in emulsions made by the hot dispersion route is investigated. The compositions used are set out in Table 12a and the testing results in Table 12b below. As expected, generally the inclusion of the water soluble additives and co-solvents reduced the stability of the emulsions. The oil soluble chemical sunfilters in Examples 12.9 to 12.11 had little if any adverse effect on emulsion stability. Water soluble sunfilters were not included in these tests because they are generally ionic and would thus destabilise the emulsion. In 12.12 a physical sunfilter (titanium dioxide) was used, but as the dispersant for the titanium dioxide is a sodium polyacrylate dispersant, the electrolyte affected the stability of the emulsion. This was separately confirmed by including amounts as small as 0.1% by weight of conventional polyacrylate dispersants in emulsions using the emulsifier stabiliser system of the invention and finding that emulsion stability was substantially reduced.

TABLE 12a

| Ex No | EM3 (wt %) | PS 1 (wt %) | Additives type | (wt %) | Oil 1 (wt %) | Pre 1 (wt %) | water (wt %) |
|---|---|---|---|---|---|---|---|
| 12.1 | 0.05 | 0.05 | Add 6 | 5 | 20 | 1 | to 100 |
| 12.2 | 0.05 | 0.05 | Add 7 | 5 | 20 | 1 | to 100 |
| 12.3 | 0.05 | 0.05 | Add 8 | 10 | 20 | 1 | to 100 |
| 12.4 | 0.05 | 0.05 | Add 1 | 10 | 20 | 1 | to 100 |
| 12.5 | 0.05 | 0.05 | Add 9 | 5 | 20 | 1 | to 100 |
| 12.6 | 0.05 | 0.05 | Add 10 | 10 | 20 | 1 | to 100 |
| 12.7 | 0.05 | 0.05 | Add 11 | 5 | 20 | 1 | to 100 |
| 12.8 | 0.05 | 0.05 | Add 12 | 5 | 20 | 1 | to 100 |
| 12.9 | 0.05 | 0.05 | Add 13 | 3 | 20 | 1 | to 100 |
| 12.10 | 0.05 | 0.05 | Add 14 | 3 | 20 | 1 | to 100 |
| 12.11 | 0.05 | 0.05 | Add 15 | 3 | 20 | 1 | to 100 |
| 12.12 | 0.05 | 0.1 | Add 16 | 10 | 20 | 1 | to 100 |

TABLE 12b

| Ex No | pH | Viscosity (mPa s) | Stability Amb | 5° C. | 40° C. | 50° C. | Comments |
|---|---|---|---|---|---|---|---|
| 12.1 | 6.6 | 1733 | 1 M | 2 M | 1 W | 1 W | |
| 12.2 | 4.6 | 1133 | >3 M | >3 M | 1 W | 0 | |
| 12.3 | 7.0 | 1466 | >3 M | >3 M | >3 M | 2 M | |
| 12.4 | 6.5 | 2900 | >3 M | >3 M | >3 M | 2 M sl translucent | |
| 12.5 | 6.4 | 1366 | 2 M | >3 M | 2 M | 2 M | |

TABLE 12b-continued

| Ex No | pH | Viscosity (mPa s) | Stability Amb | 5° C. | 40° C. | 50° C. | Comments |
|---|---|---|---|---|---|---|---|
| 12.6 | 6.6 | 2933 | >3 M | >3 M | >3 M | >3 M | sl translucent |
| 12.7 | 6.3 | 1666 | 2 M | 2 M | 2 M | 1 M | |
| 12.8 | 5.6 | 1333 | 1 M | 2 M | 2 W | 1 W | |
| 12.9 | 6.3 | 2800 | >3 M | >3 M | >3 M | 3 M | |
| 12.10 | 6.3 | 1633 | >3 M | >3 M | >3 M | 3 M | |
| 12.11 | 6.3 | 3066 | >3 M | >3 M | >3 M | >3 M | |
| 12.12 | 7.8 | 1833 | 1 W | 1 M | 1 M | 1 W | |

EXAMPLE 13

In this Example emulsions were made by the hot dispersion route using various grades of *Konjak* and Xanthan in combinations as the emulsion stabiliser. The compositions are given in Table 13a and testing results in Table 13b below.

TABLE 13a

| Ex No | EM 3 (wt %) | Stabilier type | (wt %) | Oil 1 (wt %) | Pre I (wt %) | Water (wt %) |
|---|---|---|---|---|---|---|
| 13.1 | 0.05 | PS 1 | 0.05 | 20 | 1 | to 100 |
| 13.2 | 0.05 | PS 3 | 0.05 | 20 | 1 | to 100 |
| 13.3 | 0.05 | PS 4 | 0.05 | 20 | 1 | to 100 |
| 13.4 | 0.05 | PS 5 | 0.05 | 20 | 1 | to 100 |
| 13.5 | 0.05 | PS 6 | 0.05 | 20 | 1 | to 100 |
| 13.6 | 0.05 | PS 7 | 0.05 | 20 | 1 | to 100 |
| 13.7 | 0.05 | PS 8 | 0.05 | 20 | 1 | to 100 |
| 13.8 | 0.05 | PS 9 | 0.05 | 20 | 1 | to 100 |
| 13.9 | 0.05 | PS 10 | 0.05 | 20 | 1 | to 100 |

TABLE 13b

| Ex No | pH | Viscosity (mPa·s) | Stability Amb | 5° C. | 40° C. | 50° C. | Comments state | appear | stability |
|---|---|---|---|---|---|---|---|---|---|
| 13.1 | 6.8 | 1833 | >3 M | >3 M | >3 M | >3 M | v liquid milk | 1 | v good |
| 13.2 | 6.7 | 1766 | >3 M | >3 M | >3 M | >3 M | v liquid milk | 2 | v good |
| 13.3 | 6.7 | 3133 | >3 M | >3 M | >3 M | >3 M | v liquid milk | 3 | v good |
| 13.4 | 6.6 | 1700 | >3 M | >3 M | >3 M | 2 M | v liquid milk | 2 | medium |
| 13.5 | 5.8 | 3900 | >3 M | >3 M | >3 M | 1 M | v liquid milk | 3 | medium |
| 13.6 | 6.5 | 2800 | >3 M | >3 M | >3 M | 3 M | v liquid milk | 3 | good |
| 13.7 | 6.7 | 2133 | >3 M | >3 M | >3 M | 2 M | v liquid milk | 1 | good |
| 13.8 | 6.2 | 1466 | >3 M | >3 M | >3 M | 2 W | v liquid milk | 1 | medium |
| 13.9 | 6.7 | 1400 | >3 M | >3 M | >3 M | 2 W | v liquid milk | 1 | medium |

EXAMPLE 14

A milk emulsion was made up by the cold dispersion route using a citrate trans ester as a low HLB emulsifier. The composition and testing results are set out in Table 14 below.

TABLE 14

| | amounts (wt %) | | | | | Viscosity | stability | |
|---|---|---|---|---|---|---|---|---|
| Ex No | PS 7 | EM 5 | EM 11 | Pre 1 | Oil 1 | Water | (mPa·s) | Amb | 50° C. |
| 14.1 | 0.1 | 0.4 | 0.5 | 1 | 20 | to 100 | 1600 | >1 W | >1 W |

EXAMPLE 15

In this Example a number of creams were made up using different types of thickener. The basic emulsion formulation was 20 wt % Oil 1, 1 wt % Pre 1, 0.9 wt % emulsifier/emulsion stabiliser an amount of the various thickeners indicated in Table 15 below and water to 100 wt %. The emulsifier stabiliser system was based on a combination of 1 part by weight of PS 1 as emulsion stabiliser, 6 parts by weight EM 8 as high HLB emulsifier and 2 parts by weight of EM 10 as low HLB emulsifier. In the comparative runs, the polysaccharide stabiliser was omitted, but the emulsifiers were included. Runs 15.1, 15.1.C, 15.3 and 15.3.C used the hot dispersion route and runs 15.2 and 15.2.C used the cold dispersion route. Variable formulation information and testing results are given in Table 15 below.

TABLE 15

| | Thickener | | Viscosity | | Stability | | Comments | |
|---|---|---|---|---|---|---|---|---|
| Ex No | type | (wt %) | (mPa·s) | pH | Amb | 50° C. | state | skin feel |
| 15.1 | TH 1 | 2 | 25400 | 7.6 | >1 M | >1 M | milk | 1 |
| 15.1.C | TH 1 | 2 | 14660 | 7.7 | 2 W | 1 W | fluid milk | 3 |
| 15.2 | TH 7 | 1 | 34200 | 7.0 | >1 M | >1 M | milk | 2* |
| 15.2.C | TH 7 | 1 | 16530 | 7.0 | 3 W | 0 | fluid milk | 3 |
| 15.3 | TH 2 | 3 | 16530 | 6.7 | >1 M | >1 M | milk | 1** |
| 15.3.C | TH 2 | 3 | 18730 | 6.7 | >1 M | 0 | fluid milk | 3 |

*slightly sticky
**stringy

EXAMPLE 16

A range of emulsion compositions was made up using the emulsifier stabiliser composition used in Example 15, the basic emulsion having the following composition:

| Oil Phase | Aqueous phase |
|---|---|
| Oil 7 4 | PS 7 0.1 |
| Oil 8 1 | EM 8 0.6 |
| Oil 2 1 | EM 10 0.2 |
| Oil 6 2 | Add 1 4 |
| Oil 5 1 | Pre 2 0.7 |
| | Water to 100 |

The viscosity of the compositions was varied by the inclusion of thickening components. In the sequence from 16.1 to 16.4 the viscosity increases from that of a fluid milk to a cream with all compositions being derived from the same basic emulsion. Runs 16.1 used the cold dispersion route and runs 16.2, 16.3 and 16.4.C used the hot dispersion route to aid incorporation of the added thickening components (which are solid at ambient temperature). The thickening components and the results of testing are indicated in Table 16 below. Compositions 16.1 and 16.2 were fluid milks and 16.3 and 16.4 were creams. All the compositions had a light skin feel, had very good spreading properties and good stability.

TABLE 16

| | Thickeners (amount wt %) | | | Viscosity | | Stability | |
|---|---|---|---|---|---|---|---|
| Ex No | TH 2 | TH 3 | TH 11 | (mPa·s) | pH | Amb | 50° C. |
| 16.1 | 0 | 0 | 0 | 4700 | 6.5 | >6 M | >2 M |
| 16.2 | 1 | 1 | 0 | 7300 | 5.7 | >6 M | >2 M |
| 16.3 | 4 | 3 | 0 | 39000 | 5.0 | >6 M | >2 M |
| 16.4 | 4 | 3 | 3 | 54830 | 4.6 | >6 M | >2 M |

EXAMPLE 17

This Example illustrates emulsions with variations in oil concentration, including high and low oil concentration emulsions, made using varying proportions of emulsifier and polysaccharide stabiliser using the cold dispersion method. The emulsifier/emulsion stabiliser composition (ES 17) used included 2 parts by weight EM 1, 13 parts by weight EM 5, 2 parts by weight EM 11 and 2 parts by weight PS 7. Emulsions were made up by the cold emulsification route using 5% (Ex No 17.1), 20% (Ex No 17.2) and 40% (Ex No 17.3) by weight Oil 1, 1% Pre 1 and 0.25% (runs 'a'), 0.5% (runs 'b'), 0 75% (runs 'c') and 1% (runs 'd') of the ES 17 with water to 100% by weight. The results of viscosity and stability testing are set out in Table 17 below. The flexibility of the emulsifier stabiliser system of the invention is clear even though no attempt was made to optimise the formulation for the particular oil content or amount of emulsion stabiliser used.

TABLE 17

| Ex No | Viscosity (mPa·s) | Stability Amb | 5° C. | 40° C. | 50° C. |
|---|---|---|---|---|---|
| 17.1a | 570 | >2 M | >2 M | >2 M | 1 M |
| 17.1b | 1033 | >2 M | >2 M | >2 M | 2 M |
| 17.1c | 1266 | >2 M | >2 M | >2 M | >2 M |
| 17.1d | 2083 | >2 M | >2 M | >2 M | 1 M |
| 17.2a | 467 | >2 M | >2 M | >2 M | 1 M |
| 17.2b | 900 | >2 M | >2 M | >2 M | 2 M |
| 17.2c | 1366 | >2 M | >2 M | >2 M | >2 M |
| 17.2d | 2033 | >2 M | >2 M | >2 M | 2 M |
| 17.3a | 400 | >2 M | >2 M | >2 M | 2 M |
| 17.3b | 1033 | >2 M | >2 M | >2 M | 2 M |
| 17.3c | 1800 | >2 M | >2 M | >2 M | >2 M |
| 17.3d | 2460 | >2 M | >2 M | >2 M | 1 M |

EXAMPLE 18

This Example illustrates emulsions with very high oil concentration and their dilution to typical cosmetic use concentrations. A base formulation having the following composition was made up by the hot dispersion route:

| | parts | | parts |
|---|---|---|---|
| Oil 1 | 80 | EM 11 | 0.2 |
| PS 7 | 0.2 | Pre 1 | 1 |
| EM 5 | 1.3 | water | 17 |
| EM 1 | 0.2 | | |

This base formulation emulsion had a viscosity of 128500 mPa.s. Various dilutions (cold) with water (including additional preservative) were made and tested. These formulations and the test results are set out in Table 18 below. The diluted emulsions were very thin (near water thin) milks show some signs of separation of an aqueous phase during storage especially at high temperature, but without signs of the emulsion breaking. This contrasts with Example 17 where low oil emulsions directly made up did not show this sort of separation.

TABLE 18

| Ex No | base (wt %) | Pre 1 (wt %) | Water (wt %) | stability amb | 50° C. |
|---|---|---|---|---|---|
| 18.1 | 50 | 0.5 | 49 | >1 W | 1 W |
| 18.2 | 25 | 0.7 | 74 | >1 W | 2 W |
| 18.3 | 15 | 1 | 84 | >1 W | 2 W |

EXAMPLE 19

Using an emulsifier stabiliser (ES 19) containing 0. 1 parts PS 7, 0.65 parts EM 5, 0.1 parts EM 1 and 0.1 parts EM 11, various high oil content emulsions were made up, using the cold dispersion route, and tested. The formulations are summarised and the test results set out in Table 18 below. These data indicate that highly concentrated emulsions can be made within the invention having at least moderate stability.

TABLE 19

| Ex No | ES 19 (wt %) | Oil 1 (wt %) | Pre 2 (wt %) | water (wt %) | Visc (mPa·s) | stability amb | 50° C. |
|---|---|---|---|---|---|---|---|
| 18.1 | 0.95 | 50 | 1 | 48 | 6400 | >1 W | >1 W |
| 18.2 | 0.95 | 60 | 1 | 38 | 11600 | >1 W | >1 W |
| 18.3 | 0.95 | 70 | 1 | 28 | 27700 | >1 W | >1 W |
| 18.4 | 0.95 | 80 | 1 | 18 | 75000 | >1 W | >1 W |

EXAMPLE 20

This example illustrates the use of emulsions of the invention in makeup removers. So called "waterproof mascara" is used as a test material for makeup removal because it is usually based on water insoluble oils and represents a hard target for makeup removers. Neat oils are effective removers, with non-polar oils being generally better than polar oils, but in practical use, neat oils tend to leave the skin greasy. Generally emulsion formulations are less effective than neat oils and oil in water emulsions are generally less effective than water in oil emulsions. This is believed to be because water in oil emulsions have the oil in the external (continuous) phase so the oil is in direct contact with the makeup.

The test involves coating artificial skin with the mascara and attempting to remove it using a pad impregnated with the remover composition worked across the artificial skin with a mechanical arm. The extent of removal is measured by the difference in reflectance (delta) of the skin before and after removal of the mascara. Tests are run in sets of replicates and the results quoted below are the mean and standard deviation of the measured deltas. The ability of various compositions to remove "waterproof mascara" was assessed. Three formulation types were tested with two types of oil: Oil 3 is a low polarity oil and Oil 14 is a medium polarity oil. Neat oil formulations and oil in water emulsions emulsified and stabilised with EM 4 (a mixture of high and low HLB alcohol ethoxylates) were used for comparison with oil in water emulsion s of the invention emulsified and stabilised by the formulation used in Example 19.

TABLE 20

| Ex No | Oil type | Oil amount | Emulsifier type | Emulsifier amount | Add 1 | Pre 2 | Water | Delta | SD |
|---|---|---|---|---|---|---|---|---|---|
| 20.C.1 | Oil 2 | 100 | — | — | — | — | — | 57.4 | 6.2 |
| 20.C.2 | Oil 14 | 100 | — | — | — | — | — | 53.5 | 5.3 |
| 20.C.3 | Oil 2 | 20 | EM4 | 5 | 4 | 0.7 | to 100* | 36.2 | 5 |
| 20.C.4 | Oil 14 | 20 | EM4 | 5 | 4 | 0.7 | to 100* | 28.4 | 7.9 |
| 20.1 | Oil 2 | 20 | ES19 | 1 | 4 | 0.7 | to 100 | 51.4 | 3.5 |
| 20.1 | Oil 14 | 20 | ES19 | 1 | 4 | 0.7 | to 100 | 48.2 | 4.2 |

*0.1 parts of a thickener (Carbopol 2050) was included to increase the viscosity of the emulsion enough to test it on the artificial skin.

These results show that the emulsions using EM 4 are much less effective than the neat oils, although, because the continuous phase is aqueous, there is much reduced tendency to a greasy afterfeel. The emulsions of the invention are comparable in effectiveness of mascara removal to the neat oils and largely avoid the greasy afterfeel.

EXAMPLE 21

This example illustrates the preparation of suspoemulsions in which an oil in water emulsion further includes dispersed pigment. The components of the formulations are set out in Table 21a below. The suspoemulsions were made up as follows:

The pigments were mixed and pre-ground in a laboratory grinder. The water was heated to 80° C. and the sugar surfactant (EM 12) and the polymeric stabiliser (PS 11) were dispersed in the water with stirring. The thickener (TH 4) was added and the mixture subjected to intensive stirring for 5 minutes. The glycerin and preservative were then added and mixed in followed by the dispersion of the pigments in the water phase under intensive stirring. The oil phase was prepared by heating the oil components to 80° C. including oil soluble emulsifier (if used). The oil phase was added to the water phase with stirring and the formulation was homogenised for 2 minutes using an Ultra-Turrax mixer (at ca. 10000 rpm; ca 170 Hz) and the mixture was allowed to cool to ambient temperature under stirring.

TABLE 21a

| Ex No | PS 11 | EM 12 | EM 10 | Th 4 | Oil 10 | Add 1 | Add 17 | Pre 2 | Water |
|---|---|---|---|---|---|---|---|---|---|
| 21.1 | 0.05 | 0.95 | — | 2 | 20 | 4 | 12.65 | 0.7 | to 100 |
| 21.1 | 0.05 | 0.95 | 2 | 3 | 20 | 4 | 12.65 | 0.7 | to 100 |

Example 21.1 was a fluid milk which had good pigment dispersion and a very nice skin feel. Example 21.2 was a viscous cream which had good pigment dispersion and a very nice skin feel. Some properties and outline storage stability data are given in Table 21.b below TABLE 21b

| | | Viscosity | | 40° C. | Amb | 5° C. |
|---|---|---|---|---|---|---|
| Ex No | pH | (mPa · s) | spindle | 1M | 1M | 1M |
| 21.1 | 6.9 | 9500 | RV3 | NS | NS | NS |
| 21.2 | 6.9 | 50700 | RV5 | NS | NS | NS |

EXAMPLE 22

An emulsion was made up for use in tissue impregnation. The components of the formulation are given in Table 22a below. The emulsion was made by the hot process with the polymeric stabiliser (PS7) and preservative in the water phase and the emulsifiers (EM 1 and EM 3) in the oil (paraffin liquid) phase.

TABLE 22a

| Ex No | PS 7 | EM 1 | EM 3 | Pre 2 | Oil 11 | water |
|---|---|---|---|---|---|---|
| 22.1 | 0.05 | 0.475 | 0.475 | 0.7 | 5 | to 100 |

The emulsion was a very fluid white milk which was well suited for tissue impregnation. Some properties and outline storage stability data are given in Table 22.b below.

TABLE 22

| | | Viscosity | | 40° C. | Amb | 5° C. |
|---|---|---|---|---|---|---|
| Ex No | pH | mPa · s | spindle | 1M | 1M | 1M |
| 22.1 | 6.5 | 1400 | RV3 | NS | NS | NS |

EXAMPLE 23

This Example illustrates suspoemulsions with physical sunscreens as the suspended solid phase. In Example 23a, Examples 23.1 to 23.4 are of oil in water spray sunscreen milks with physical sunfilters and, in Example 23b, Examples 23.5 to 23.8 are of oil in water sunscreen milks using predispersed physical sunfilters. The compositions of the formulations and their measured viscosities are set out in Tables 23.a and 23b below. The formulations of Examples 23.1 to 23.4 were made up by the cold process except that the oil phase, which included the EM 1 and EM 2 emulsifiers, was warmed just enough to melt the emuslifiers, using the following procedure:

the polymeric stabiliser was dispersed in the water and stirred until homogeneous, the thickener (TH 4) was then added and under stirring until homogeneous. The titanium dioxide (Add 18) was then added and stirred to give uniform dispersions and the other additive (Add 9) and preservative were added under stirring. The oil components (Oil 2 and Oil 3) and emulsifiers EM1 and EM 2 were mixed and warmed to melt the emulsifiers and the oil phase was added slowly to the water phase to give a homogeneous mixture. The mixture was homogenised for 2 minutes and then stirred until the emulsion was uniform.

TABLE 23a

| Ex No | Stabiliser type | (%) | EM 1 | EM 2 | Oil 2 | Oil 3 | Th 4 | Add 9 | Add 18 | Water | Visc (mPa · s) |
|---|---|---|---|---|---|---|---|---|---|---|---|
| 23.1 | PS12 | 0.1 | 0.7 | 0.2 | 8 | 4 | 1 | 4 | 3.2 | to 100 | 1960 |
| 23.2 | PS13 | 0.1 | 0.7 | 0.2 | 8 | 4 | 1 | 4 | 3.2 | to 100 | 2040 |
| 23.3 | PS14 | 0.1 | 0.7 | 0.2 | 8 | 4 | 1 | 4 | 3.2 | to 100 | 2190 |
| 23.4 | PS15 | 0.1 | 0.7 | 0.2 | 8 | 4 | 1 | 4 | 3.2 | to 100 | 2680 |

The formulations of Examples 23.5 to 23.9 were made up by the following procedure:

The water was heated to 80° C. and the other water phase components (polymeric stabiliser and emulsifier EM 13) were added and the water phase maintained at 80° C. for 30 minutes with stirring (to swell the emulsifier). The mixture was then homogenised for 30 seconds (using a PowerGen 720 homogeniser at speed setting 5.5; 8750 rpm ca 145 Hz). The oil phase was made up separately by heating the mixed oil phase components (Oil 3, Oil 9, Add 19 and Add 20) to 80° C. under stirring. The oil phase was then added to the water phase while stirring gently The mixture was then emulsified by homogenisation, above 65° C., for 1 minute (using a PowerGen 720 homogeniser at speed setting 6; 10000 rpm ca 1 70 Hz) and then allowed to cool to ambient temperature under slow stirring.

The compositions used and the viscosity of the emulsions are set out in Table 23b below:

TABLE 23b

| Ex No | Stabiliser type | (%) | EM 13 | Oil 3 | Oil 9 | Add 19 | Add 20 | Water | Visc (mPa · s) |
|---|---|---|---|---|---|---|---|---|---|
| 23.5 | PS12 | 0.1 | 0.9 | 2.5 | 1.25 | 7.5 | 2.5 | to 100 | 11700 |
| 23.6 | PS13 | 0.1 | 0.9 | 2.5 | 1.25 | 7.5 | 2.5 | to 100 | 8300 |
| 23.7 | PS14 | 0.1 | 0.9 | 2.5 | 1.25 | 7.5 | 2.5 | to 100 | 15000 |
| 23.3 | PS15 | 0.1 | 0.9 | 2.5 | 1.25 | 7.5 | 2.5 | to 100 | 10100 |

All the emulsions were stable, showing no signs separation, after 1 week storage at 4° C., ambient temperature, 46° C. and through freeze thaw cycling (−5° C./40° C.; 3 cycles).

EXAMPLE 24

This Example frustrates an emulsion of the invention including an insect repellent. The polymeric stabiliser was dispersed in the water with stirring until homogeneous and the remaining water phase components (emulsifiers, EM 15 and EM 16) were then added with stirring. The oil phase components (emulsifier EM 14, Oil 9, Oil 3, Oil 12, Add 21 and Add 22) were mixed and then added slowly to the aqueous phase with stirring. The mixture was then homogenised for 2 minutes and the mixture stirred gently until the emulsion was homogeneous at which point the preservative was added. The compositions used and the viscosity of the emulsions are set out in Table 24 below:

TABLE 24

| | Stabiliser | | | | | | | | | | | Visc |
|---|---|---|---|---|---|---|---|---|---|---|---|---|
| Ex No | type | (%) | EM 14 | EM 15 | EM 16 | Oil 9 | Oil 3 | Oil 12 | Add 21 | Add 22 | Pre 1 | Water | (mPa · s) |
| 24.1 | PS12 | 0.1 | 0.32 | 0.4 | 0.18 | 2 | 1 | 2 | 15 | 0.2 | 1 | to 100 | 2240 |
| 24.2 | PS13 | 0.1 | 0.32 | 0.4 | 0.18 | 2 | 1 | 2 | 15 | 0.2 | 1 | to 100 | 2940 |
| 24.3 | PS14 | 0.1 | 0.32 | 0.4 | 0.18 | 2 | 1 | 2 | 15 | 0.2 | 1 | to 100 | 2350 |
| 24.4 | PS15 | 0.1 | 0.32 | 0.4 | 0.18 | 2 | 1 | 2 | 15 | 0.2 | 1 | to 100 | 2220 |

All the emulsions were stable, showing no signs separation, after 1 week storage at 4° C., ambient temperature, 46° C. and through freeze thaw cycling (−5° C./40° C.; 3 cycles) although after the first freeze thaw cycle, a slight trace of oil was visible on top of the emulsion, but this has got no worse on subsequent cycles.

The multiple emulsion was made be mixing the secondary oil phase (Oil 2, Oil 12 and Oil 3) and dissolving the polymeric emulsifier (EM 17) in the oil blend by stirring and heating to 40 to 45° C. The primary emulsion was slowly added to the secondary oil phase under moderate stirring and the mixture was homogenised for 1 minute at 9500 rpm with an Ultra-Turrax blender The emulsion was then gently stirred until a homogeneous appearance was obtained.

The composition of the multiple emulsion is set out in Table 25.

TABLE 25a

| | Multiple emulson components | | | | | | | | Multiple Oil in water in oil emisions | | | | |
|---|---|---|---|---|---|---|---|---|---|---|---|---|---|
| Ex | Primary oil in water emulsion | | | | | | | | Primary | External Oil Phase Components | | | |
| No | PS 16 | Add 1 | Pre 2 | EM 3 | Oil 12 | Oil 13 | Oil 14 | water | emulsion | EM 18 | Oil 2 | Oil 12 | Oil 3 |
| 25.1 | 0.1 | 3 | 0.7 | 0.9 | 10 | 5 | 5 | to 100 | 75 | 3.5 | 10.5 | 5.5 | 5.5 |

| | | | | | | | | | | Multiple Oil in water in water in oil emulsion | | | |
|---|---|---|---|---|---|---|---|---|---|---|---|---|---|
| | Primary oil in water emulsion | | | | | | | | | Primary | External Oil Phase Components | | |
| | PS 16 | EM 1 | EM 5 | EM 11 | Add 1 | Pre 2 | Oil 12 | Oil 13 | Oil 14 | water | emulsion | EM 17 | Oil 2 Oil 3 | Oil 12 |
| 25.2 | 0.1 | 0.1 | 0.7 | 0.1 | 3 | 0.7 | 10 | 5 | 5 | to 100 | 50 | 3.5 | 23.5 11.5 | 11.5 |
| 25.3 | 0.1 | 0.1 | 0.7 | 0.1 | 3 | 0.7 | 10 | 5 | 5 | to 100 | 75 | 3.5 | 10.5 5.5 | 5.5 |

EXAMPLE 25

This Example illustrates oil in water in oil (OWO) multiple emulsion made according to the invention. The multiple emulsions were made by first making a primary oil in water emulsion stabilised according to the invention and subsequently emulsifying this into an external oil phase. The water soluble or dispersible components, polymeric stabiliser (PS16) glycerol (Add 1) and preservative (Pre 1), were gradually added to the water with stirring (speed 800–1000 rpm) and stirring was continued for about 10 minutes to completely disperse these components and the aqueous mixture was heated to 80° C.

The oil phase components (Oil 12, Oil 13, Oil 14 and EM 3) were mixed and heated to 70° C. and this oil phase added to the aqueous phase under stirring (speed 800–1000 rpm). The mixture was homogenised for 2 minutes at high speed using an Ultra-Turrax (+/−10000 rpm) and more gentle stirring was continued for several minutes Stir for some minutes (speed 800–1000 rpm) until the emulsion appearance was homogeneous and the emulsion was allowed to cool to ambient temperature under stirring to RT.

The emulsion viscosities were measured (spindle RV3) and the storage stability assessed and the results are set out in Table 25b below.

TABLE 25b

| | | Storage Stability | | | | |
|---|---|---|---|---|---|---|
| | | 40° C. | | Amb | | |
| Ex No. | Visc. (mPa.s) | 1 D | 1 W | 1 D | 1 W | 1 M |
| 25.1 | <100 | NS | NS | NS | NS | NS |
| 25.2 | <100 | NS | NS | NS | NS | NS |

All the emulsions were very liquid low viscosity emulsions.

Microscopic examination with a Jenalumar microscope using a lambda filter and magnification 1000× showed that the emulsion contained oil in water droplets and droplets that appear to be aqueous droplets (without visible oil droplets in them).

EXAMPLE 26

This Example illustrates water in oil in water (WOW) multiple emulsion made according to the invention.

The water in oil primary emulsion was made by separately mixing and heating to about 75° C. the aqueous phase components (water and Pre 1) and the oil phase components (EM 17, Oil 2, Oil 3 and Oil 12), slowly adding the aqueous phase to the oil phase under gentle stirring, homogenising for 1 minute and then allowing the water in oil emulsion to cool to about 40° C. under gentle stirring, again homogenising and then allowing the emulsion to cool to ambient temperature under gentle stirring. The multiple emulsions were made by adding the surfactant (EM 1, EM 5 and EM 7) to the water with gentle stirring, then add the EM 18 and continue the stirring for about 10 minutes, the polymeric stabiliser (PS 16) was added, the mixture heated to 80° C. and homogenised for 2 minutes. The primary emulsion was then added under moderate stirring, followed by the preservative and a second low energy homogenisation was carried out and the emulsion stirred until homogeneous and allowed to cool to ambient temperature.

TABLE 26a

Multiple emulson components

| | Primary water in oil emulsion | | | | | Primary | Multiple Oil in water in oil emulsion | | | | | | |
| | | | | | | | | External Aqueous phase | | | | | |
| Ex No | EM 17 | Oil 2 | Oil 3 | Oil 12 | Pre 1 | Water | emulsion | PS 16 | EM 1 | EM 5 | EM 7 | EM 18 | Pre 1 | water |
|---|---|---|---|---|---|---|---|---|---|---|---|---|---|---|
| 26.1 | 3.5 | 15 | 7.5 | 7.5 | 1 | to 100 | 40 | 0.1 | 0.2 | 0.7 | — | — | 1 | to 100 |
| 26.2 | 3.5 | 15 | 7.5 | 7.5 | 1 | to 100 | 20 | 0.1 | 0.2 | 0.7 | — | — | 1 | to 100 |
| 26.3 | 3.5 | 15 | 7.5 | 7.5 | 1 | to 100 | 60 | 0.1 | — | — | — | 0.9 | 1 | to 100 |
| 26.4 | 3.5 | 15 | 7.5 | 7.5 | 1 | to 100 | 60 | 0.1 | — | — | 0.9 | 0.9 | 1 | to 100 |
| 26.5 | 3.5 | 15 | 7.5 | 7.5 | 1 | to 100 | 60 | 0.1 | — | — | 0.9 | 0.5 | 1 | to 100 |

The emulsion viscosities were measured (spindle RV3) and the storage stability of the emulsions was assessed and the results are given in Table 26b below. Microscopic examination of the emulsion (as in Example 25) showed clearly that the majority of the droplets were water in oil emulsion droplets.

TABLE 26b

| | Storage Stability | | | | | | | | | |
| | 50° C. | | | 40° C. | | | Amb | | | Visc |
| Ex No | 1 D | 1 W | 1 M | 1 D | 1 W | 1 M | 1 D | 1 W | 1 M | (mPa.s) |
|---|---|---|---|---|---|---|---|---|---|---|
| 26.1 | NS | NS | NS | NS | NS | NS | NS | NS | NS | <100 |
| 26.2 | NS | NS | NS | NS | NS | NS | NS | NS | NS | <100 |
| 26.3 | NS | NS | NS | NS | NS | NS | NS | NS | NS | <100 |
| 26.4 | NS | NS | NS | NS | NS | NS | NS | NS | NS | <100 |
| 26.5 | NS | NS | NS | NS | NS | NS | NS | NS | NS | <100 |

What is claimed is:

1. A personal care or cosmetic oil-in-water emulsion in the form of a milk or cream comprising: at least one oil, water; and an emulsifier stabilizer system composed of
   (a) from 0.02 to 1.5 by weight of the emulsion of total oil emulsifier component, wherein the oil emulsifier component comprises at least one or more non-ionic emulsifier(s) selected from the group consisting of at least one alkoxylate emulsifiers, fatty acid esters, ethers, hemi-acetals of polyhydroxylic compounds, acetals of polyhydroxylic compounds, and a fatty acids amides which are N-substituted with the residue of a polyhydroxylic compound, and
   (b) a polysaccharide combination of a Xanthan polysaccharide and a polyglucomannan polysaccharide which is present from 0.02 to 0.5% by weight of the emulsion.

2. The emulsion as claimed in claim 1, wherein the polyglucomannan polysaccharide comprises random glucose/mannose backbone at a molar ratio of glucose to mannose of from 1:1.5 to 1:3.

3. The emulsion as claimed in claim 1, wherein the polyglucomannan polysaccharide is a polyglucomannan derived from *Konjak*.

4. The emulsion as claimed in claim 1, wherein the weight ratio of Xanthan to polyglucomannan is from 1:10 to 10:1.

5. The emulsion as claimed in claim 4, wherein the weight ratio of Xanthan to polyglucomannan is from 2:1 to 1:2.

6. The emulsion as claimed in claim 1, wherein the non-ionic emulsifier is at least one alkoxylate emulsifiers.

7. The emulsion as claimed in claim 6, wherein the oil emulsifier component is at least one alcohol ethoxylates.

8. The emulsion as claimed in claim 1, wherein the non-ionic emulsifier is at least one fatty acid esters.

9. The emulsion as claimed in claim 8, wherein the emulsion comprises one or more sugars selected from the group consisting of sucrose, fructose and glucose.

10. The emulsion of claim 8 wherein said fatty acid esters are saccharide esters of fatty acids and a sugar, with a mono-ester content of at least 60%.

11. The emulsion as claimed in claim 1, wherein the oil emulsifier component comprises at least one alkoxylate emulsifier with an average of from 10 to 100 alkylene oxide residues and having an HLB greater than 12 and the amount of emulsifier used is from 0.04 to 0.1% by weight of the emulsion.

12. The emulsion as claimed in claim 1, wherein the oil emulsifier component includes at least one hydrophilic non-ionic emulsifier having an HLB of at least 12 and at least one hydrophobic non-ionic emulsifier having an HLB of less than 8.

13. The emulsion as claimed in claim 12, wherein the hydrophilic emulsifier comprises at least one of alkoxylate emulsifiers with an average of from 10 to 100 alkylene oxide residues; sugar mono-esters; polyglycerol mono-esters; hydrocarbyl polysaccharides; fatty acid glycerol esters where the fatty acid has 8 to 12 carbon atoms; and fatty acid N-sugar amides, and wherein the hydrophobic emulsifier comprises at least one of alkoxylate emulsifiers with an average of from 2 to about 10 alkylene oxide residues; glycerol esters where the fatty acid has 14 to 24 carbon atoms; and anhydrosaccharide fatty acids.

14. The emulsion as claimed in claim 13, wherein the amount of the hydrophilic emulsifier is from 0.04 to 0.5% by weight of the emulsion and the amount of the hydrophobic emulsifier is from 0.1 to 1% by weight of the emulsion.

15. The emulsion as claimed in claim 1, wherein the oil phase comprises an emollient oil.

16. The emulsion as claimed in claim 15, wherein the emollient oil comprises at least one normally liquid emollient oil selected from the group consisting of mineral oils, paraffin oils, vegetable glyceride oils, animal glyceride oils, synthetic ester oils, synthetic ether oils, silicone oils, fatty alcohol propoxylates, a solid liquefiable emollient fat, a solid liquefiable emollient wax, and mixtures thereof.

17. The emulsion as claimed in claim 1, wherein the oil phase is at least 5% by weight of the emulsion.

18. The emulsion as claimed in claim 1 in the form of a cream comprising at least one thickener selected from fatty amphiphiles or synthetic thickeners.

19. The emulsion as claimed in claim 1 comprising:
from 1 to 80% by weight of at least one oil;
   from 0.02 to 1.2% by weight of at least one alkoxide emulsifier having an HLB of at least 12;
   optionally from 0.1 to 1.2% by weight of at least one emulsifier having an HLB of less than 8;
   the total amount of emulsifier being from 0.02 to 1.5% by weight;
from 0.02 to 0.5% by weight of at least one polysaccharide stabilizer; optionally from 0.1 to 10% by weight of at least one thickener selected from fatty amphiphiles or synthetic thickeners;
   the remainder being minor components and additives and water.

20. The emulsion as claimed in claim 1 comprising:
from 1 to 80% by weight of at least one oil;
   from 0.02 to 1.2% by weight of at least one emulsifier having an HLB of at least 12 selected from the group consisting of a fatty acid ester, ether, hemi-acetal or acetal of a polyhydroxylic compound, and a fatty acid amide which is N-substituted with the residue of a polyhydroxylic compound;
   optionally from 0.1 to 1.2% by weight of at least one emulsifier having an HLB of less than 8;
   the total amount of emulsifier being from 0.02 to 1.5% by weight;
from 0.02 to 0.5% by weight of at least one polysaccharide stabilizer;
   optionally from 0.1 to 10% by weight of at least one thickener selected from fatty amphiphiles or synthetic thickeners;
   the remainder being minor components and additives and water.

21. The emulsion as claimed in claim 1 having a pH of from 4 to 9.

22. The emulsion as claimed in claim 1 comprising one or more of: preservatives; perfumes; humectants or solvents; sunfilter or sunscreen materials; alpha hydroxy acids; self-tanning agents; antimicrobial components; Vitamins and their precursors; skin care agents; phospholipids; vesicle-containing formulations; germanium-containing compounds; botanical extracts; skin whiteners; skin repair compounds; caffeine; cooling additives; insect repellents; essential oils; and pigments.

23. A method of making an emulsion as claimed in claim 1 by direct emulsification, wherein the emulsifier(s) and polysaccharide stabilizer are incorporated into the aqueous phase, optionally including thickener components in the aqueous phase, and then mixing the oil into the aqueous continuous phase to emulsify it.

24. The method as claimed in claim 23, wherein the polysaccharide stabilizer in the aqueous phase is heated to above about 60° C. and is optionally subjected to high intensity mixing.

25. The method of making an emulsion as claimed in claim 1 by inverse emulsification, wherein the emulsifier(s) and polysaccharide stabilizer are incorporated into the oil phase and the aqueous phase is then mixed into the oil phase until the system inverts to form an oil-in-water emulsion.

26. The method as claimed in claim 25, wherein the polysaccharide stabilizer in contact with the aqueous phase is heated to above about 60° C., and is optionally subjected to high intensity mixing.

27. The emulsion as claimed in claim 1, wherein the polysaccharide combination of a Xanthan polysaccharide and a polyglucomannan polysaccharide is present from 0.025 to 0.15% by weight of the emulsion.

28. The emulsion as claimed in claim 1, wherein the non-ionic emulsifier is at least one fatty acid amide that is N-substituted with the residue of a polyhydroxylic compound.

29. An emulsion as claimed in claim 1, wherein the amount of oil emulsifier component is from 0.1 to 1.5% by weight of the emulsion.

30. The emulsion of claim 1 wherein said oil emulsifier component is present in the amount of 0.02% by weight of the emulsion.

31. The emulsion of claim 1 wherein said oil emulsifier component is present in the amount of 1.5% by weight of the emulsion.

32. The emulsion of claim 1 wherein said polysaccharide combination of a Xanthan polysaccharide and a polyglucomannan polysaccharide which is present in the amount of 0.02% by weight of the emulsion.

33. The emulsion of claim 1 wherein said polysaccharide combination of a Xanthan polysaccharide and a polyglucomannan polysaccharide which is present in the amount of 0.5% by weight of the emulsion.

34. The emulsion of claim 1 wherein said oil emulsifier component is present in an amount of from 0.02 to 0.25% by weight of the emulsion, and wherein said polysaccharide combination of a Xanthan polysaccharide and a polyglucomannan polysaccharide is present in an amount from 0.02 to 0.25% by weight.

35. A personal care or cosmetic oil-in-water emulsion with good body and skin feel in the form of a milk or cream comprising: at least one oil; water; and an emulsifier stabilizer system composed of
(a) from 0.02 to 1.5% by weight of the emulsion of total oil emulsifier component, wherein the emulsifier comprises at least one or more non-ionic emulsifier(s) selected from the group consisting of at least one alkoxylate emulsifiers, fatty acid esters, ethers, hemi-acetals of polyhydroxylic compounds, acetals of polyhydroxylic compounds, and a fatty acid amides which are N-substituted with the residue of a polyhydroxylic compound, and
(b) a polysaccharide combination of a Xanthan polysaccharide and a polyglucomannan polysaccharide which is present from 0.02 to 0.5% by weight of the emulsion.

36. The emulsion as claimed in claim 35, wherein the polyglucomannan polysaccharide is a polyglucomannan derived from *Konjak*.

37. The emulsion as claimed in claim 35, wherein the non-ionic emulsifier is at least one alkoxylate emulsifiers.

38. The emulsion as claimed in claim 35, wherein the non-ionic emulsifier is at least one fatty acid ester.

39. The emulsion as claimed in claim 35, wherein the oil phase is at least 5% by weight of the emulsion.

40. The emulsion as claimed in claim 35 in the form of a cream comprising at least one thickener selected from fatty amphiphiles or synthetic thickeners.

41. The emulsion as claimed in claim 35, wherein the non-ionic emulsifier is at least one fatty acid amide that is N-substituted with the residue of a polyhydroxylic compound.

42. An emulsion as claimed in claim 35, wherein the amount of said oil emulsifier component is from 0.1 to 1.5% by weight of the emulsion.

43. The emulsion of claim 35 wherein said oil emulsifier component is present in an amount of from 0.02 to 0.25% by weight of the emulsion, and wherein said polysaccharide combination of a Xanthan polysaccharide and a polyglucomannan polysaccharide is present in an amount from 0.02 to 0.25% by weight.

* * * * *